US008029458B2

(12) United States Patent
Cherif-Cheikh et al.

(10) Patent No.: US 8,029,458 B2
(45) Date of Patent: Oct. 4, 2011

(54) DEVICE FOR THE INJECTION OF A SOLID OR SEMI-SOLID IMPLANT

(75) Inventors: Roland Cherif-Cheikh, Barcelona (ES); Christophe Aubert, Cudrefin (CH); Thierry Rimlinger, L'Isle d'Abeau (FR); Fabrice Bonacci, Saint Priest (FR); Serge Barneaud, Puget Theniers (FR)

(73) Assignee: Sociétéde Conseils de Recherches et d'Applications Scientifiques (S.C.R.A.S.) SAS, Paris (FR)

( * ) Notice: Subject to any disclaimer, the term of this patent is extended or adjusted under 35 U.S.C. 154(b) by 294 days.

(21) Appl. No.: 11/720,542

(22) PCT Filed: Nov. 15, 2005

(86) PCT No.: PCT/EP2005/012247
§ 371 (c)(1),
(2), (4) Date: Apr. 10, 2009

(87) PCT Pub. No.: WO2006/058613
PCT Pub. Date: Jun. 8, 2006

(65) Prior Publication Data
US 2009/0209903 A1 Aug. 20, 2009

(30) Foreign Application Priority Data
Dec. 1, 2004 (EP) .................................. 04028413

(51) Int. Cl.
*A61B 17/20* (2006.01)
(52) U.S. Cl. ................ 604/47; 604/59; 604/60; 604/48; 604/218; 604/228; 604/197
(58) Field of Classification Search .................... 604/59, 604/60, 47, 48, 218, 228, 197
See application file for complete search history.

(56) References Cited
U.S. PATENT DOCUMENTS
3,016,895 A * 1/1962 Sein ................................ 604/60
(Continued)

FOREIGN PATENT DOCUMENTS
EP 0 596 162 A1 5/1994
(Continued)

OTHER PUBLICATIONS
Office Action in co-pending related U.S. Appl. No. 11/720,534, issued on Jun. 24, 2010.
(Continued)

*Primary Examiner* — Nicholas D Lucchesi
*Assistant Examiner* — Scott Medway
(74) *Attorney, Agent, or Firm* — Griffin & Szipl, P.C.

(57) ABSTRACT

The invention relates to a device which is used to inject an implant (6) into tissues (50). The inventive device is characterized in that it comprises: a main hollow body (2; 2') having a hollow needle (4; 4') fixed thereto, into which the implant (6) is introduced; a secondary body (26; 26') which is disposed coaxially inside the main body (2; 2') and which surrounds the needle (4; 4'); and a plunger rod (36; 36') which can slide coaxially inside the hollow needle (4; 4'). The injection device (1; 1') is arranged such that: (i) when it is pressed against the tissues (50), the main body (2; 2') slides along the length of the secondary body (26; 26') from a proximal position to a distal position such that the needle (4; 4') can penetrate the tissues (50), whereby the movement of the main body (1; 1') is accompanied by the concomitant movement of the plunger rod (36; 36'); and (ii) the plunger rod (36; 36') remains fixed and maintains the implant (6) at the required depth in the tissues (50) until the needle (4; 4') is removed therefrom when the main body (2; 2') is returned from the distal position to the proximal position.

43 Claims, 21 Drawing Sheets

U.S. PATENT DOCUMENTS

| | | | |
|---|---|---|---|
| 3,809,298 A * | 5/1974 | Harris et al. | 222/386 |
| 4,701,164 A * | 10/1987 | Cassou et al. | 604/218 |
| 4,850,968 A * | 7/1989 | Romano | 604/110 |
| 4,881,551 A * | 11/1989 | Taylor | 600/567 |
| 4,941,874 A * | 7/1990 | Sandow et al. | 604/60 |
| 4,950,234 A * | 8/1990 | Fujioka et al. | 604/60 |
| 5,019,049 A * | 5/1991 | Haining | 604/165.02 |
| 5,090,962 A * | 2/1992 | Landry et al. | 604/110 |
| 5,098,402 A * | 3/1992 | Davis | 604/195 |
| 5,141,500 A * | 8/1992 | Hake | 604/198 |
| 5,147,303 A * | 9/1992 | Martin | 604/110 |
| 5,176,643 A * | 1/1993 | Kramer et al. | 604/135 |
| 5,273,541 A * | 12/1993 | Malenchek | 604/110 |
| 5,284,479 A | 2/1994 | de Jong | |
| 5,300,079 A | 4/1994 | Niezink et al. | |
| 5,304,152 A * | 4/1994 | Sams | 604/207 |
| 5,370,620 A * | 12/1994 | Shonfeld | 604/110 |
| 5,522,804 A * | 6/1996 | Lynn | 604/191 |
| 5,542,920 A * | 8/1996 | Cherif Cheikh | 604/57 |
| 5,562,613 A | 10/1996 | Kaldany | |
| 5,632,729 A * | 5/1997 | Cai et al. | 604/288.01 |
| 5,695,463 A * | 12/1997 | Cherif-Cheikh | 604/60 |
| 5,823,994 A * | 10/1998 | Sharkey et al. | 604/60 |
| 5,984,890 A * | 11/1999 | Gast et al. | 604/60 |
| 6,056,726 A * | 5/2000 | Isaacson | 604/164.01 |
| 6,179,812 B1 * | 1/2001 | Botich et al. | 604/110 |
| 6,228,049 B1 | 5/2001 | Schroeder et al. | |
| 6,402,716 B1 | 6/2002 | Ryoo et al. | |
| 6,478,768 B1 * | 11/2002 | Kneer | 604/60 |
| 6,478,790 B2 * | 11/2002 | Bardani | 604/891.1 |
| 6,605,073 B1 * | 8/2003 | Pressly et al. | 604/506 |
| 6,752,782 B2 * | 6/2004 | Liao | 604/110 |
| 6,896,670 B2 * | 5/2005 | Cherif Cheikh | 604/506 |
| 6,905,478 B2 * | 6/2005 | Ingram et al. | 604/110 |
| 7,329,235 B2 * | 2/2008 | Bertron et al. | 604/88 |
| 7,500,964 B2 * | 3/2009 | Shaw et al. | 604/197 |
| 2002/0161337 A1 | 10/2002 | Shaw et al. | |
| 2002/0193747 A1 * | 12/2002 | Denolly | 604/197 |
| 2003/0040699 A1 | 2/2003 | Talling et al. | |
| 2003/0125669 A1 * | 7/2003 | Safabash et al. | 604/218 |
| 2003/0233101 A1 | 12/2003 | Lubock et al. | |
| 2005/0101967 A1 | 5/2005 | Weber et al. | |
| 2005/0159709 A1 * | 7/2005 | Wilkinson | 604/197 |
| 2008/0249466 A1 | 10/2008 | Aubert et al. | |

FOREIGN PATENT DOCUMENTS

EP  0 783 342 B1  11/1998

OTHER PUBLICATIONS

International Search Report issued in corresponding application No. PCT/EP2005/012247, completed Jan. 12, 2006 and mailed Jan. 31, 2006.

\* cited by examiner

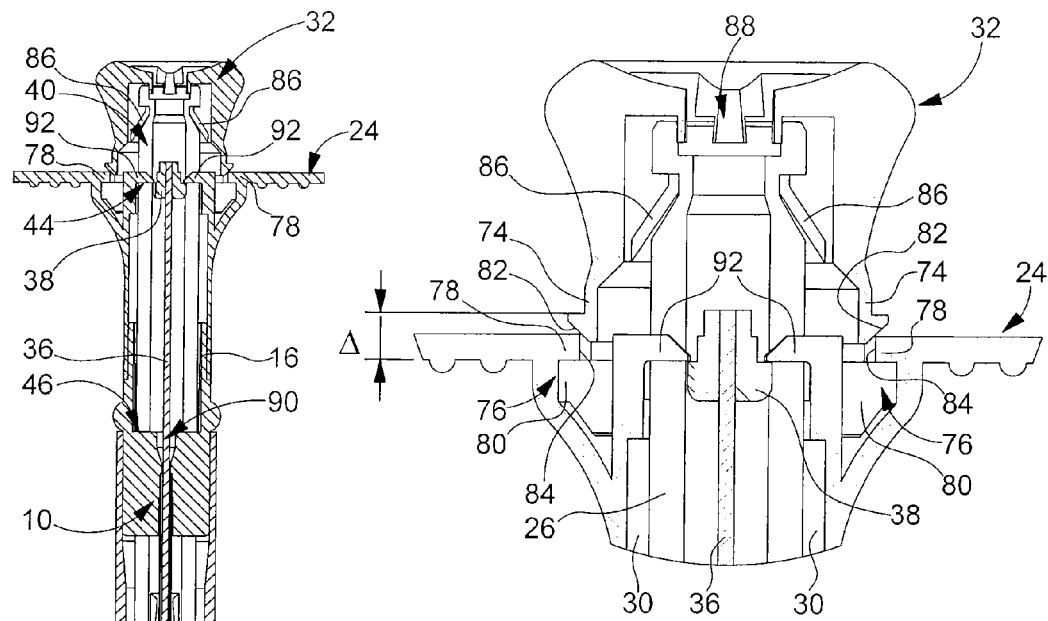
Fig. 11A
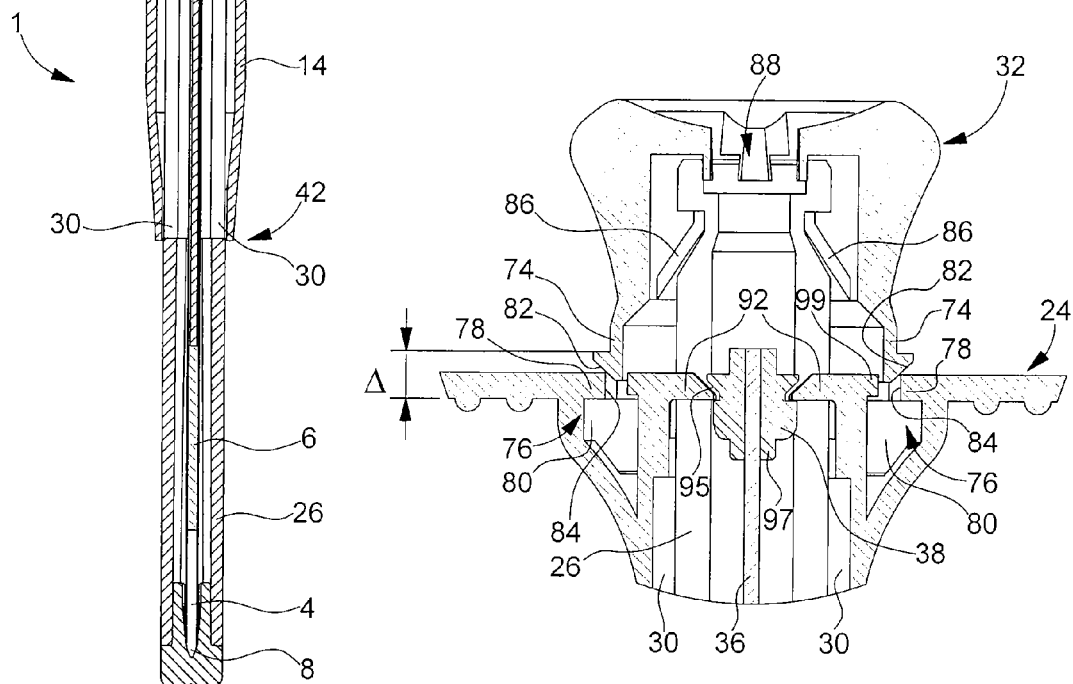
Fig. 11B
Fig. 12B

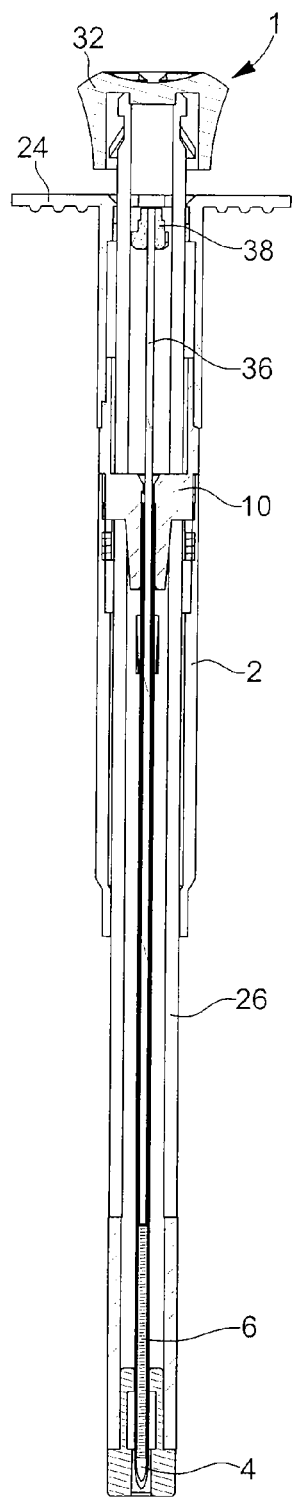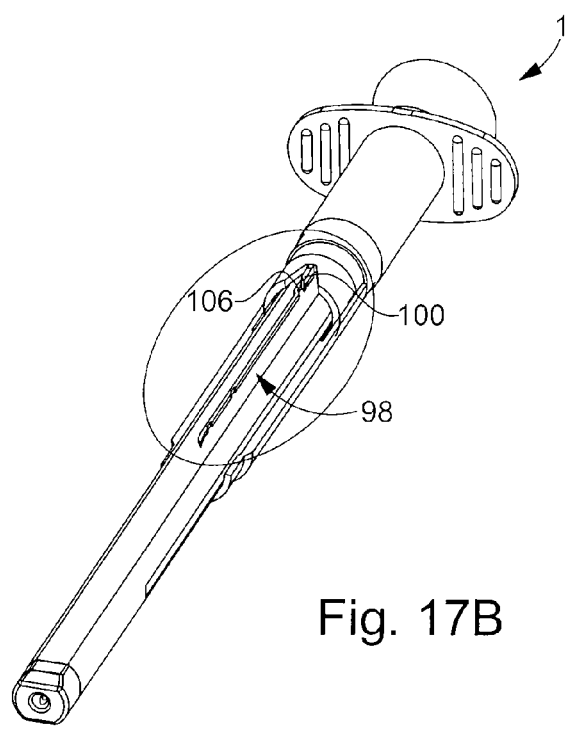
Fig. 17B
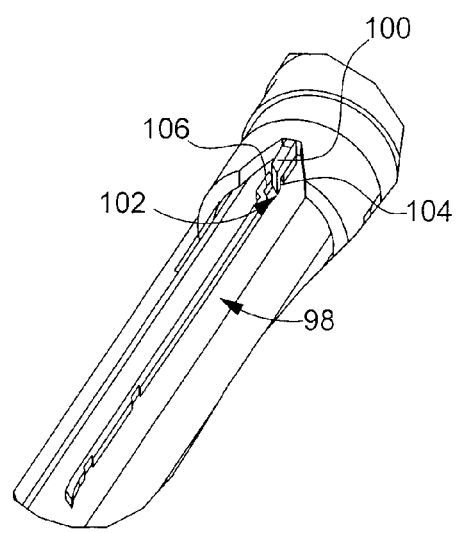
Fig. 17A
Fig. 17C

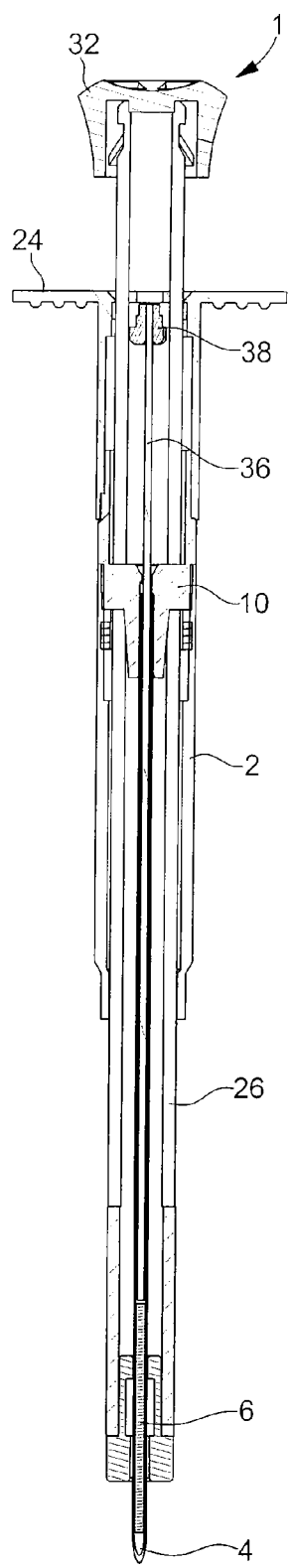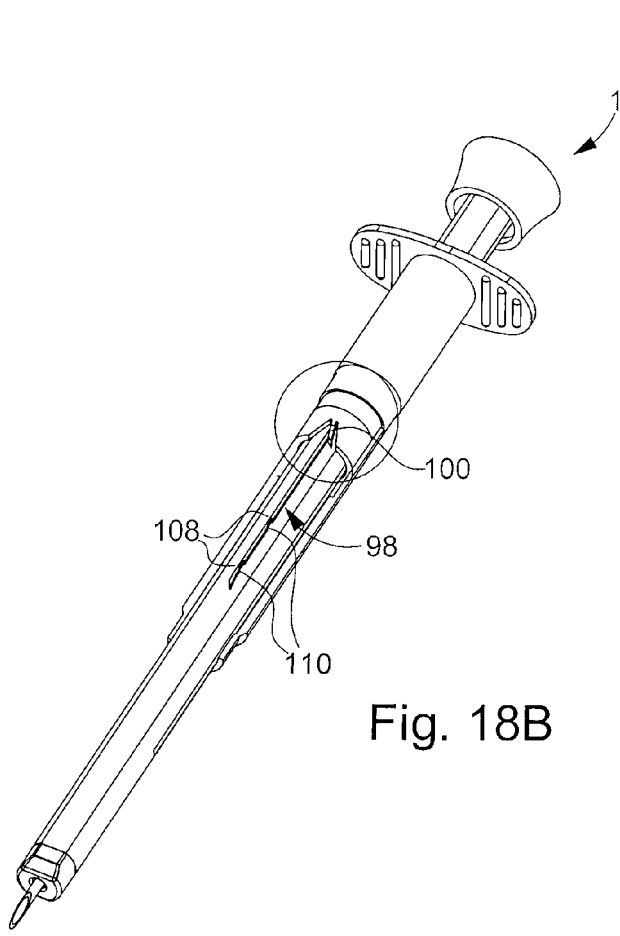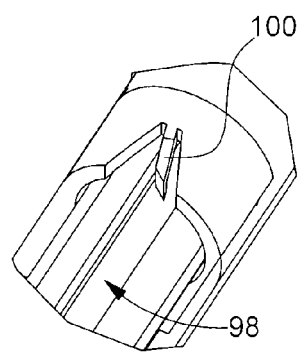
Fig. 18A
Fig. 18B
Fig. 18C

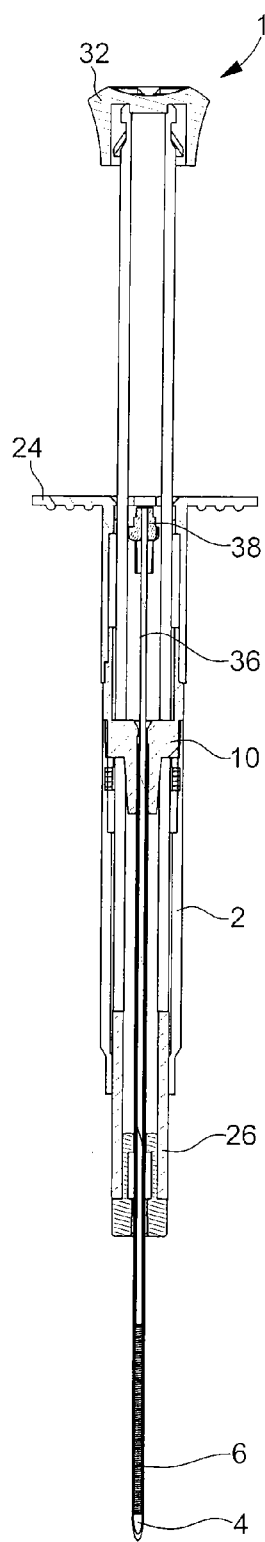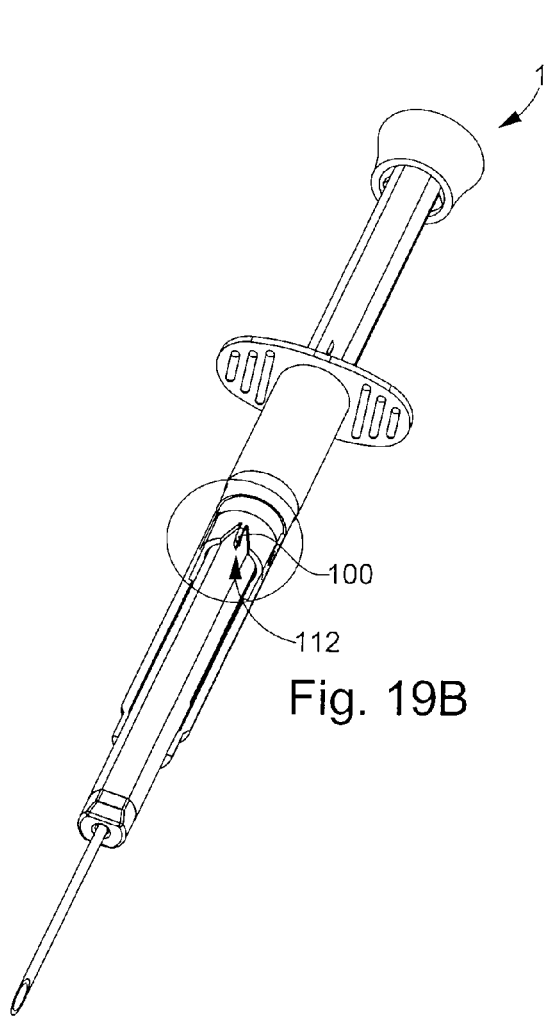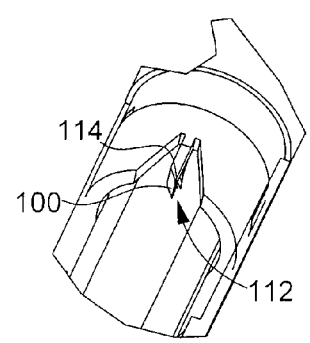
Fig. 19A
Fig. 19B
Fig. 19C

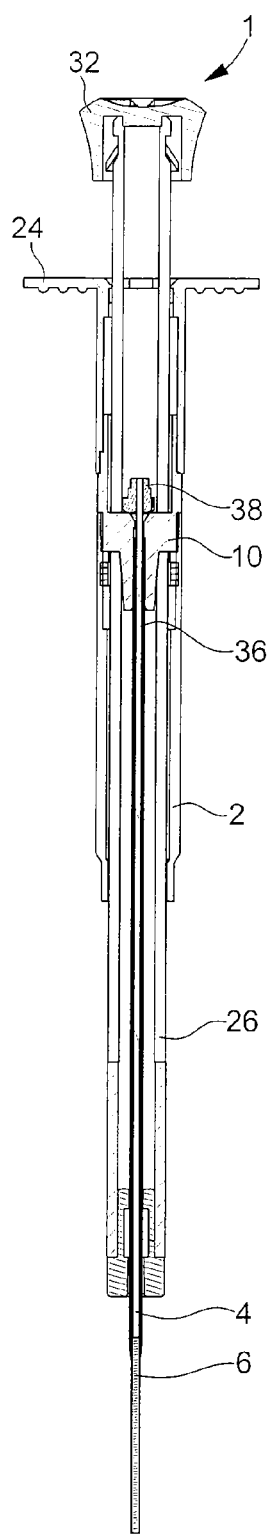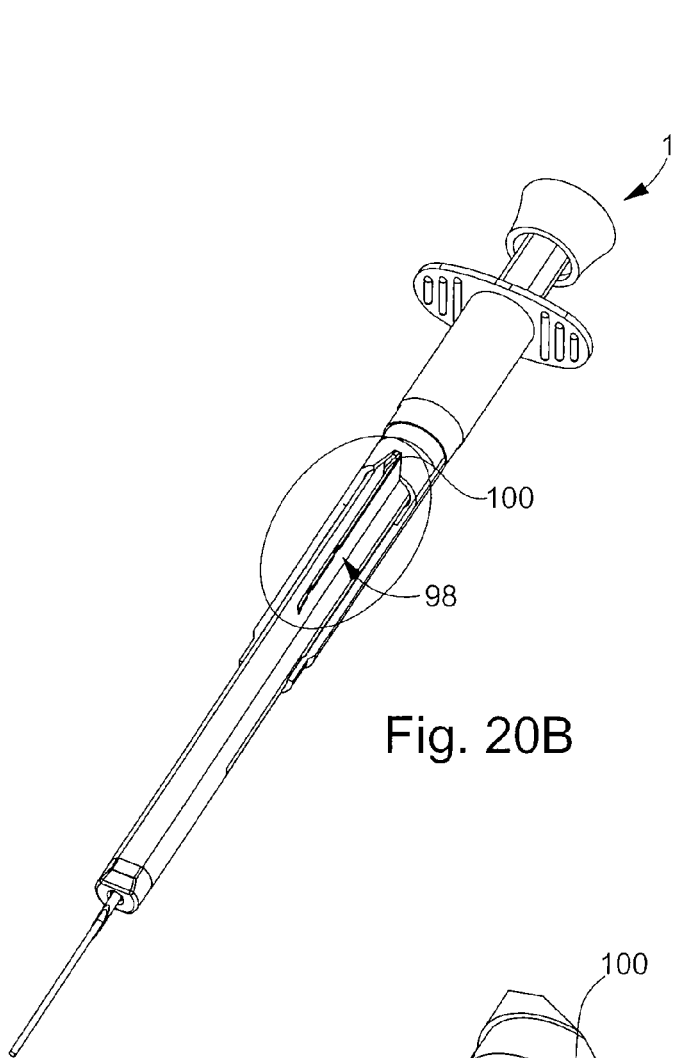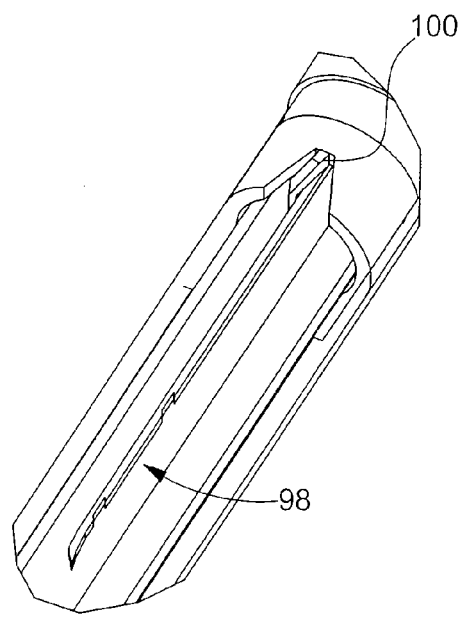
Fig. 20A
Fig. 20B
Fig. 20C

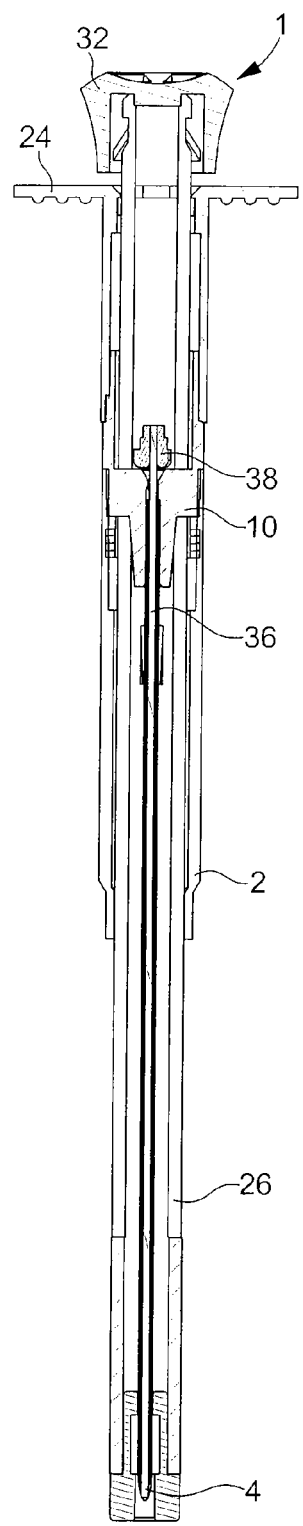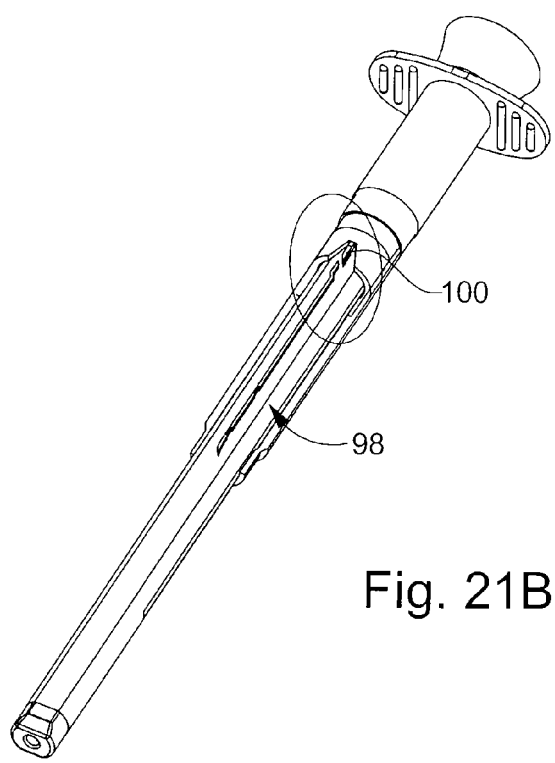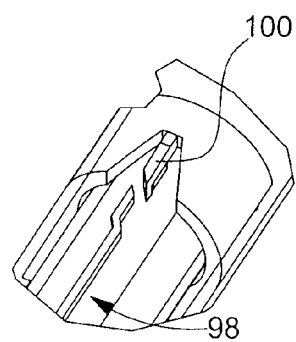
Fig. 21A
Fig. 21B
Fig. 21C

DEVICE FOR THE INJECTION OF A SOLID OR SEMI-SOLID IMPLANT

This is a National Phase Application in the United States of International Patent Application No. PCT/EP2005/012247 filed Nov. 15, 2005, which claims priority on European Patent Application No. 04028413.5, filed Dec. 1, 2004. The entire disclosures of the above patent applications are hereby incorporated by reference.

FIELD OF THE INVENTION

The present invention concerns an injection device and, in particular, a device for the intramuscular or subcutaneous injection of an active pharmaceutical principal in the solid or semi-solid state usually called an implant. More generally, the invention applies to the injection of a solid body for a human or animal, such as for example electronic chips used for the identification of a living being.

BACKGROUND OF THE INVENTION

An injection device of the aforementioned type is already known from European Patent No. EP 0 783 342 in the name of the DELAB company. This type of injection device includes a main body in two parts to which a hollow needle is fixed via a holding part. A rod is capable of sliding coaxially inside the needle and is stopped against an implant introduced into said needle. A secondary body is arranged coaxially inside the main body and surrounds the needle, such that the latter does not project prior to the injection. The secondary body includes one or several slots at different places on the length thereof, which join the two parts of the secondary body via radially extending connecting elements. The rod has a raised portion that is used as means for stopping the movement of said rod. The rod is connected to a piston, which, at the base thereof, includes a longitudinal hole. A guide element is secured to the piston and is arranged inside the main body so as to guide said piston and the rod.

One drawback of the injection device described above is that it includes a large number of parts. It is thus expensive to manufacture and difficult to assemble. Moreover, the relative movements of the constituent elements of the injection device in relation to each other are complex, which increases the risk of malfunction. Another drawback can be seen in the fact that the configuration of the injection device before and after injection is not the same, which makes this device particularly bulky and thus difficult to store.

It is an object of the present invention to overcome the aforementioned drawbacks in addition to others by providing an injection device which includes, in particular, a limited number of parts and which is thus less expensive to manufacture and easier to assemble.

SUMMARY OF THE INVENTION

The present invention therefore concerns a device for injecting an implant into live tissue, characterized in that it includes a hollow main body to which there is fixed a hollow needle, into which the implant is introduced, a secondary body arranged coaxially inside the main body and surrounding the needle and a piston rod capable of sliding coaxially inside said hollow needle, the injection device being arranged such that, when it is pressed against the tissue, said main body slides along the secondary body from a proximal position to a distal position so that the needle penetrates said tissue, the piston rod moving concomitantly and such that said piston rod remains fixed and maintains the implant at the required depth in the tissue until the needle is removed therefrom when the main body is returned from the distal position to the proximal position.

Owing to these features, the present invention provides a device for injecting an implant including a limited number of parts, and is thus less expensive to manufacture and simpler to assemble. Moreover, the configuration of the injection device is the same before and after use, the main body moving away from the proximal position towards a distal position, then returning to the initial proximal position, such that the space requirement of the injection device is limited, which facilitates packaging and storage of such devices.

According to a complementary feature of the invention, the piston rod is driven by the main body when the latter moves from its proximal position to its distal position, said piston rod being uncoupled from said main body when the latter returns from its distal position to its proximal position.

Owing to this other feature, the relative movements of the constituent parts of the injection device in relation to each other are simplified, which avoids the risk of the device malfunctioning.

According to yet another feature of the invention, the injection device includes a mechanism that avoids its locking prior to use and that allows it to be locked after use.

Thus, prior to use, it is not possible to lock the injection device inadvertently, whereas after use, the secondary body is irreversibly locked on the main body, which makes any subsequent use of the injection device according to the invention impossible. Moreover, any risk of accidental injury that could contaminate the practitioner is prevented.

BRIEF DESCRIPTION OF THE DRAWINGS

Other features and advantages of the present invention will appear more clearly from the following detailed description of the injection device according to the invention, this example being given purely by way of non limiting illustration, in conjunction with the annexed drawing, in which:

FIG. 7 is a detail view showing the uncoupling of the piston rod and the secondary body when the main body returns to its proximal position;

FIG. 11A is a longitudinal cross-section of the proximal end of the injection device according to a second embodiment allowing the implant to be loaded through the back of the injection device;

FIG. 11B is a view of a variant of the proximal end of the injection device illustrated in FIG. 11A;

FIG. 12B is a longitudinal cross-section of the injection device according to the second embodiment;

FIG. 17C is a larger scale view of the zone surrounded by a circle in FIG. 17B, which shows the position of a tongue relative to a cam path when the injection device is in its initial position prior to use as shown in the cross-section in FIG. 17A;

FIGS. 18A to 18C are similar views to FIGS. 17A to 17C, with the main body having slid along the secondary body to allow the needle to start to penetrate the skin and the tongue moving along the cam path;

FIGS. 19A to 19C are similar views to those of FIGS. 17A to 17C, with the main body having been brought to its end distal position in which the needle is completely driven into the skin and the tongue having reached the point of return;

FIGS. 20A to 20C are similar views to those of FIGS. 17A to 17C, with the main body having partially moved up along the secondary body so that the needle can be removed from the skin and the tongue moving along the opposite side of the cam path;

FIGS. 21A to 21C are similar views to those of FIGS. 17A to 17C, with the injection device in the locked position after use, the tongue having fallen into a housing provided at the end of the cam path to prevent the secondary body and the main body becoming detached;

DETAILED DESCRIPTION OF THE ILLUSTRATIVE EMBODIMENTS

The present invention proceeds from the general inventive idea that consists in providing a device for injecting a solid or semi-solid body for therapeutic or non-therapeutic purposes, which comprises a small number of parts, making assembly thereof easier and operation thereof more reliable. The present invention also concerns an injection device of this type that can be irreversibly locked after injection making any subsequent use of such device impossible and preventing any risk of accidental injury that could cause contamination.

Hereafter, the "proximal" end means the end via which the user grasps the injection device, and the "distal" end means the end of the injection device located on the side of the needle bevel.

A first embodiment of the injection device according to the invention will be described in relation to FIGS. 1 to 3B annexed to the present Patent Application.

Figure 1:
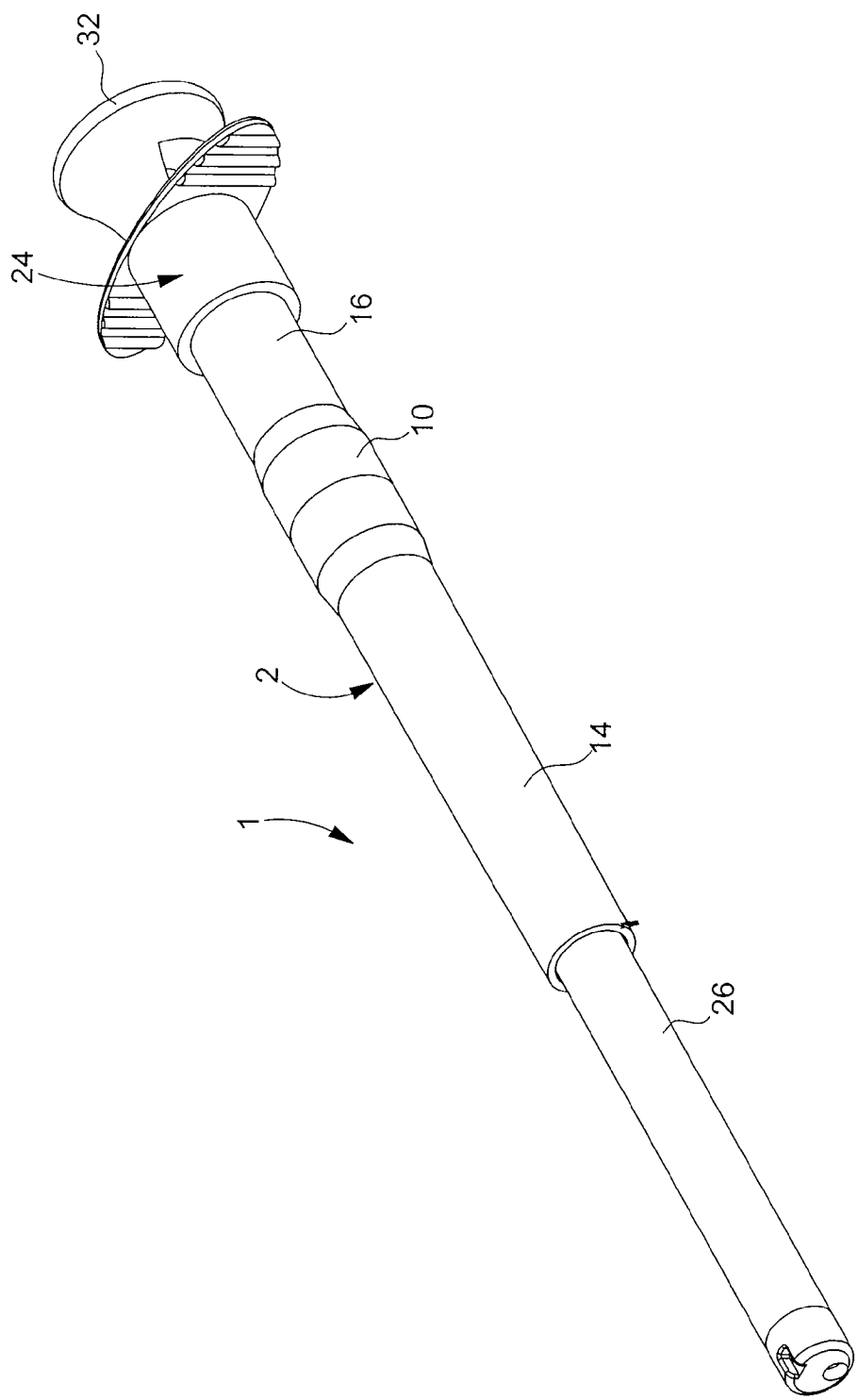
FIG. 1 is a general perspective view of the injection device according to the invention.
Figure 2:
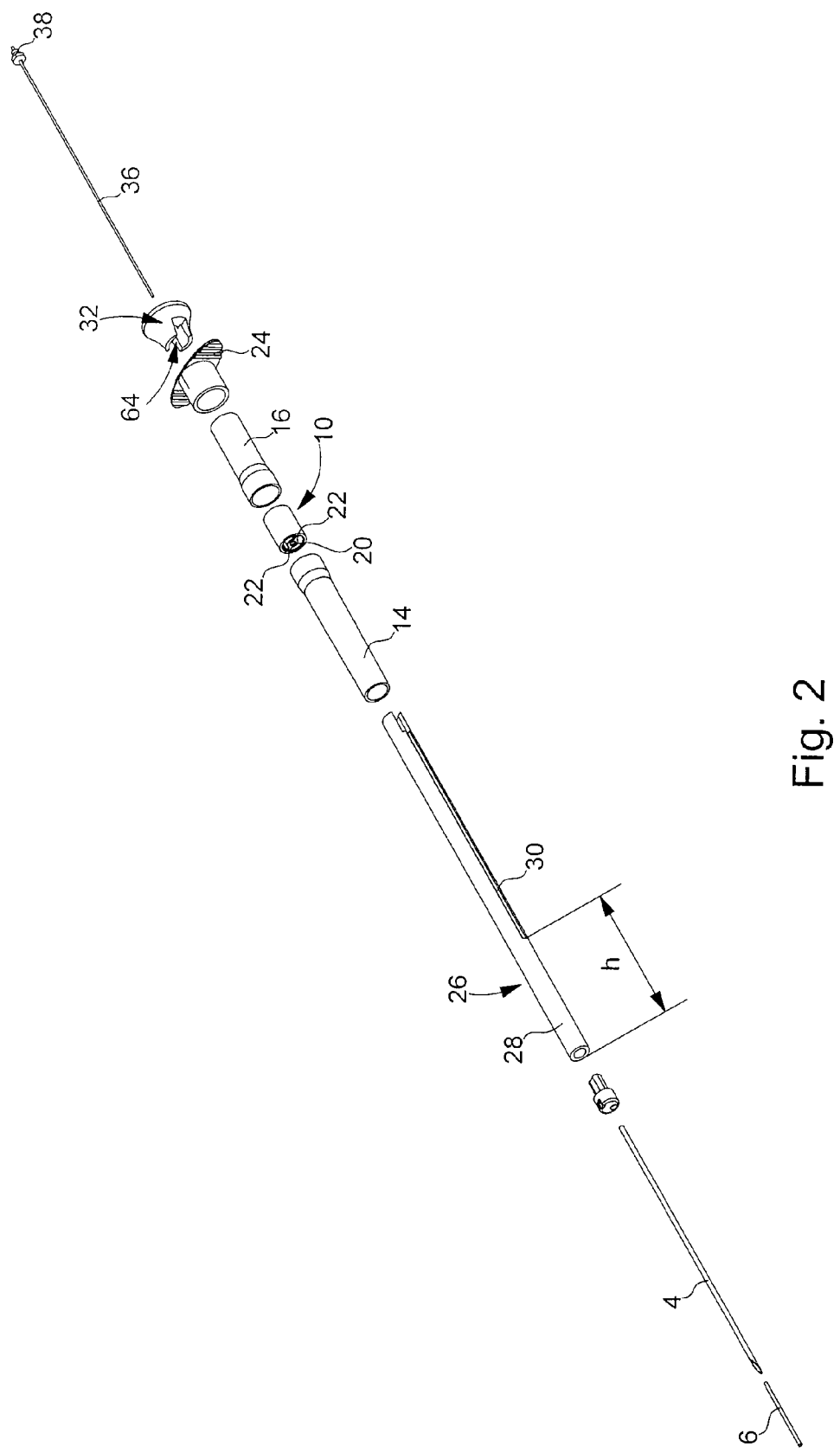
FIG. 2 is a perspective exploded view of the device of FIG. 1
Figure 3A:
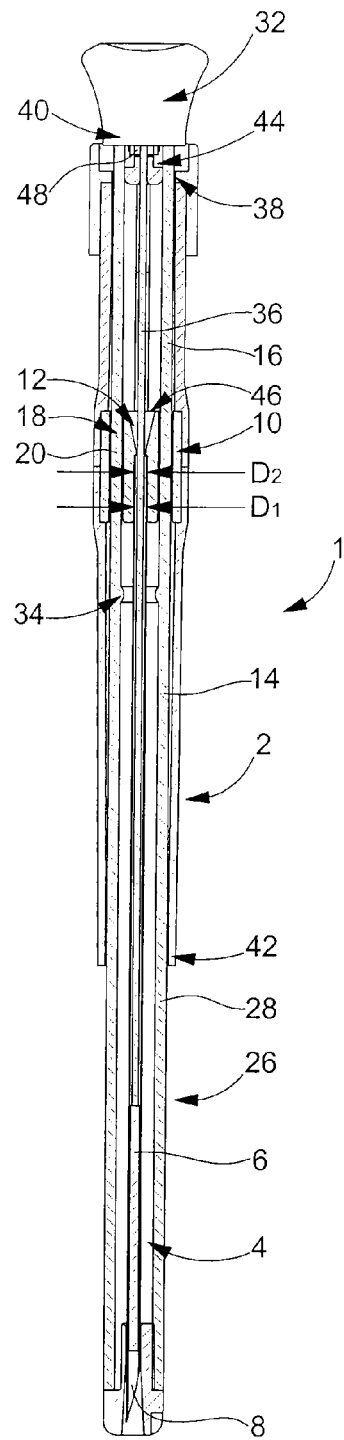
FIG. 3A is a longitudinal cross-section of the rest position of the injection device according to the invention.
Figure 3B:
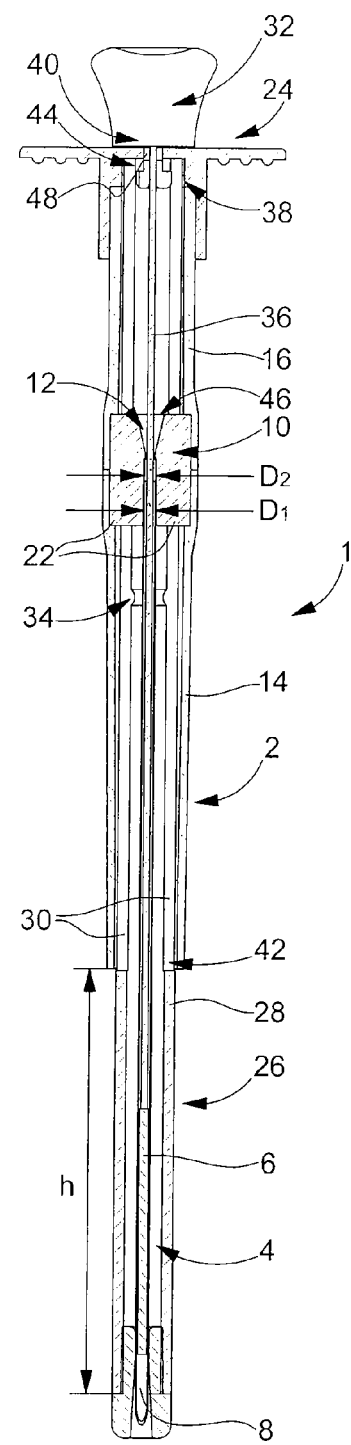
FIG. 3B is a similar view to that of FIG. 3A, with the cross-sectional plane rotated through 90°.

Designated as a whole by the general reference numeral 1, the injection device shown in cross-section in FIGS. 3A and 3B includes a hollow main body 2 to which there is permanently fixed a hollow needle 4, into which an implant 6 is introduced for injection. Implants that can be injected with a device according to the invention include both solid or semi-solid pharmaceutical compounds and other non-therapeutic implants such as, for example, electronic chips used for identifying living beings.

Preferably, hollow needle 4 has at the distal end thereof a bevel 8 whose geometry is adapted to the anticipated application of injection device 1 and, in particular, to the method of administration. At the proximal end thereof, hollow needle 4 is fixedly mounted in a holding part 10. A through aperture 12 is made in holding part 10 for mounting needle 4. This through aperture 12 has a first part of diameter $D_1$ equal to or slightly greater than the external diameter of needle 4 so that the proximal end of the latter can engage in holding part 10. The first part of diameter D1 of through aperture 12 is followed by a second part of diameter D2 smaller than the external diameter of needle 4 so that said needle can be maintained in holding part 10 by friction. This immobilisation of needle 4 could be reinforced by bonding or other means. Finally, the second part of diameter D2 of through aperture 12 is followed by a third cone-shaped part which expands in the direction of the proximal end of injection device 1 according to the invention and allows piston rod 36 to be inserted and properly guided.

According to a first variant (not shown) of the holding part 10, the latter is integral with the hollow main body 2. According to a second variant shown in the drawing, holding part 10 is used as a joining part to bottom 14 and top 16 tubular parts which form the hollow main body 2 and into which said holding part 10 is driven. In the example shown in the drawing, holding part 10 is a part of general cylindrical shape. It goes without saying that if main body 2 had, for example, to have a flat section to facilitate handling of injection device 1 and provide the practitioner with an indication as to the proper positioning of device 1 prior to injection, holding part 10 could depart from a cylindrical shape.

Figure 14:
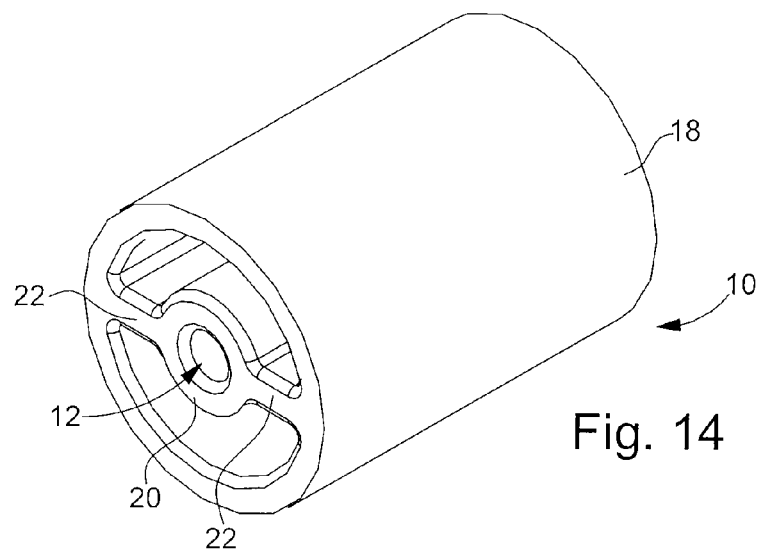
FIG. 14 is a perspective view of the holding part of the hollow needle.

Holding part 10 includes an external lateral wall 18, which delimits an inner volume into which through aperture 12 extends coaxially. Through aperture 12 is embodied by a tube portion, which is connected to external wall 18 by at least one and preferably two diametrically opposite radial ribs 22 (see also FIG. 14).

Advantageously, the proximal end of main body 2 is provided with a finger rest part 24 integral with said main body 2 or taking the form of an added part.

The hollow main body 2 is able to slide along a secondary body 26, which is also hollow, arranged coaxially inside said main body 2 and surrounding needle 4.

This secondary body 26 takes the general form of a tube 28 provided with two rectilinear slots 28 to a height h above the distal end of said tube 28, which determines the depth of penetration of needle 4. The proximal end of tube 28 will advantageously be fitted with means facilitating the grasping of injection device 1 such as a button 32. This button 32 could be integral with secondary body 26 or take the form of an added part. Finally, on the inner face of tube 28, secondary body 26 has blocking means 34, for example in the form of two raised portions whose role will be explained hereafter.

Injection device 1 according to the invention includes, finally, a piston rod 36 able to slide inside hollow needle 4 and which is used for holding implant 6 at the correct depth in the tissue. This piston rod 36 includes a head 38, which cooperates with blocking means 34 provided on secondary body 26 for uncoupling it from main body 2 as will be described in detail hereafter.

We will now examine the operating principle of injection device 1 with more particular reference to FIGS. 4A to 4D and 5A to 5D.

It will be noted first of all that main body 2 can only move between a proximal position and a distal position respectively controlled by a top stop member 40 and a bottom stop member 42 arranged on secondary body 26. In the example shown in the drawing (see in particular FIG. 3A), the top stop member is formed by button 32 against which main body 2 abuts via finger rest 24. Bottom stop member 42 is formed by the bottoms of slots 30 against which main body 2 abuts via ribs 22 when it slides axially along secondary body 26.

Likewise, piston rod 36 can only move between a proximal position and a distal position respectively controlled by a top stop member 44 and a bottom stop member 46 arranged on main body 2. In the example shown in the drawing, top stop member 44 is formed by means 48, which irreversibly block secondary body 26 onto main body 2 after injection. These means 48, which will be described in detail hereafter, can be integral with finger rest 24 if injection device 1 includes this element. The top face of holding part 10 of needle 4 forms bottom stop member 46.

Figures 4A, 4B, 4C, 4D:
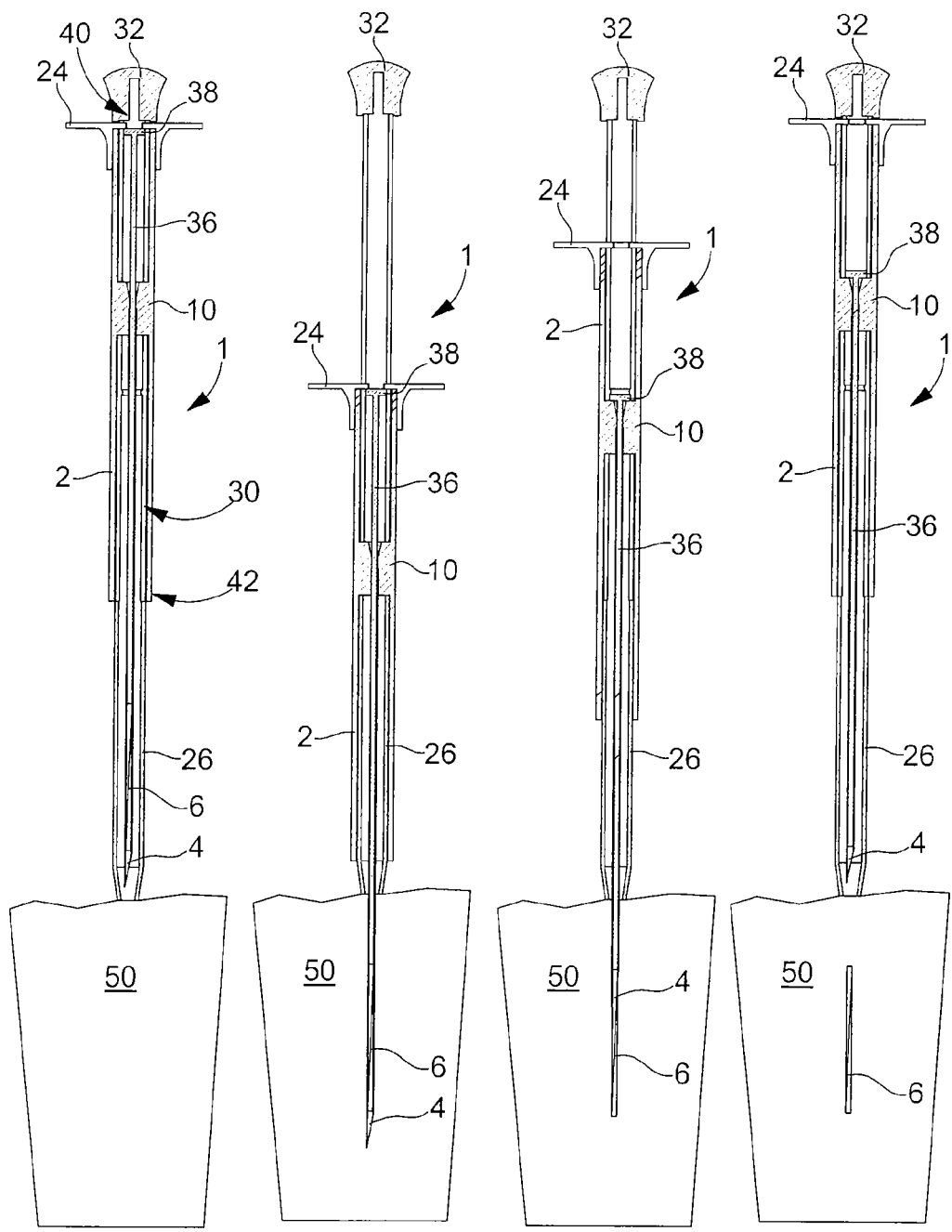
FIGS. 4A, 4B, 4C and 4D illustrate the various phases of operation of the injection device according to the invention.
Figures 5A, 5B:
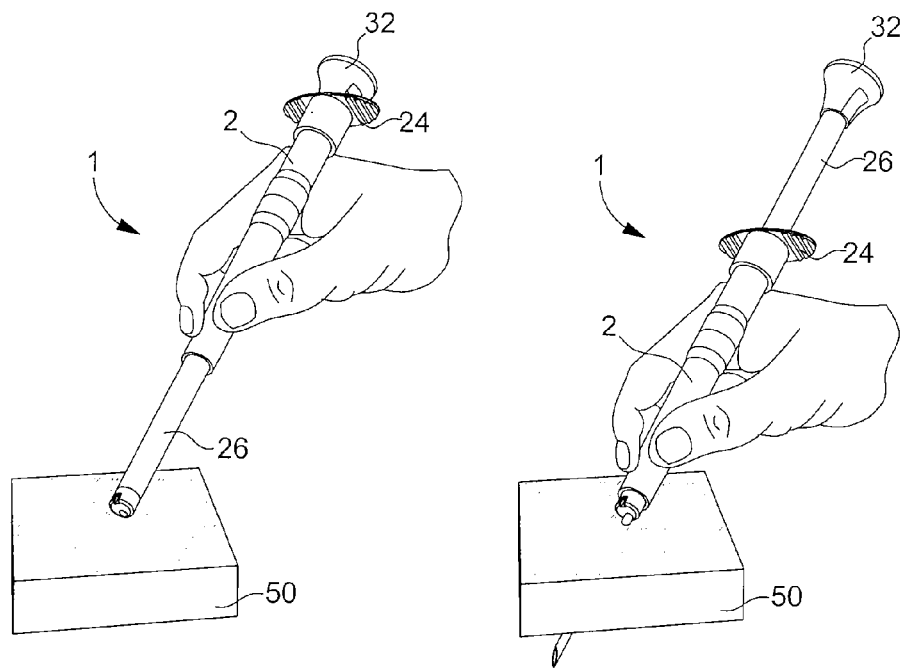
FIGS. 5A, 5B, 5C and 5D are schematic diagrams which illustrate the method of operating the injection device according to the invention.
Figure 6:
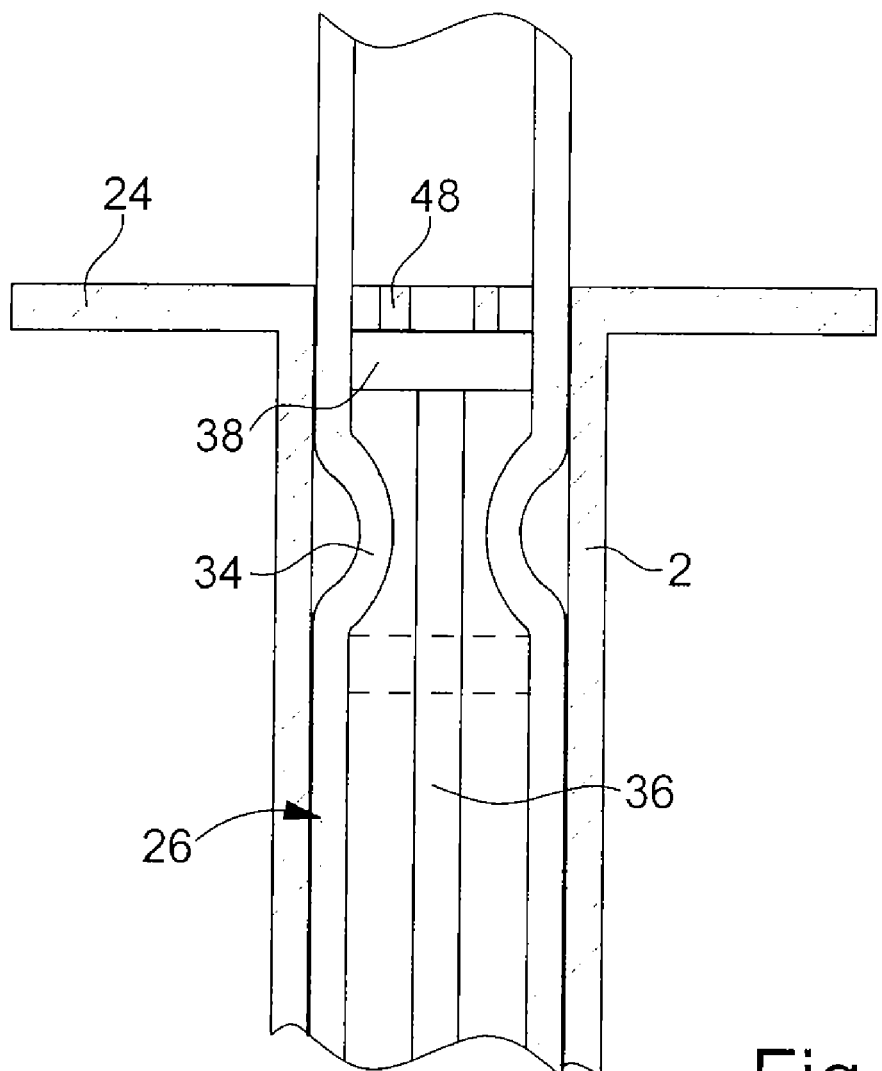
FIG. 6 is a larger scale detail view showing the coupling of the piston rod with the secondary body when the main body moves down to its distal position.

In FIGS. 4A, 5A, injection device 1 according to the invention is shown as it is delivered to the practitioner, with main body 2 occupying the proximal position in proximity to button 32 and secondary body 26 surrounding needle 4 as far as bevel 8, such that any risk of scratching is avoided. Likewise, needle 4 is hidden from the patient's view prior to the injection. By holding injection device 1 in one hand via main body 2, the practitioner presses the distal end of injection device 1 against the patient's skin 50. When injection device 1 is suitably arranged, the practitioner presses on main body 2. Via the effect of this pressure, main body 2 starts to slide axially along secondary body 26, allowing needle 4, which is secured to said main body 2, to penetrate skin 50. At the same time, main body 2 drives piston rod 36 via the bottom face of blocking means 48, such that the position of said rod 36 relative to needle 4 and implant 6 remains unchanged. Shortly before main body 2 reaches its distal end position, head 38 of piston rod 36 reaches the level of blocking means 34 carried by secondary body 26 on the bottom surface thereof and passes the latter (see FIG. 6). This movement of head 38 of piston rod 36 relative to blocking means 34 is made possible by the fact that said piston rod 36 is immobilised against the top stop member 44 arranged on main body 2 and that blocking means 34 are able to deform elastically to allow said head 38 to move past. After blocking means 34 have passed behind head 38 of piston 36, main body 2 reaches the distal end position thereof defined by radial ribs 22 which reach the bottom of slots 30. At that moment, hollow needle 4 has reached maximum penetration in the patient's skin 50 (FIGS. 4B, 5B).

It is at this stage that the actual back-injection operation of implant 6 occurs (FIGS. 4C, 5C), i.e. the delivery of said implant 6 at a determined depth independent of circumstances. Indeed, the practitioner, in a gesture not unlike that of a conventional injection, will hold injection device 1 against the patient's skin 50 with his thumb, by means of button 32, whereas, with his index and middle fingers, he will control the return of main body 2 to the proximal end position by using finger rest 24. During this movement, main body 2 slides along secondary body 26, which causes needle 4 to gradually exit the patient's skin 50. Piston rod 36 does not, however, accompany this movement of withdrawal of main body 2. In fact, retained by blocking means 34 provided on secondary body 26, piston rod 36 is uncoupled from said main body 2 and remains immobile, thereby gradually penetrating hollow needle 4 as the latter exits skin 50. Implant 6 thus emerges from needle 4, maintained in position at the correct depth in skin 50 by the distal end of piston rod 36, which is abutting against said implant 6. It will be noted that the length of piston rod 26 is such that, when needle 4 is moved relative to said piston rod 36, the latter does not move past the tip of said needle 4, but is at least flush with the heel of bevel 8 or at the very least sufficiently close to said bevel 8 that implant 6, already largely engaged in tissue 50, no longer needs the support.

Figures 5C, 5D:
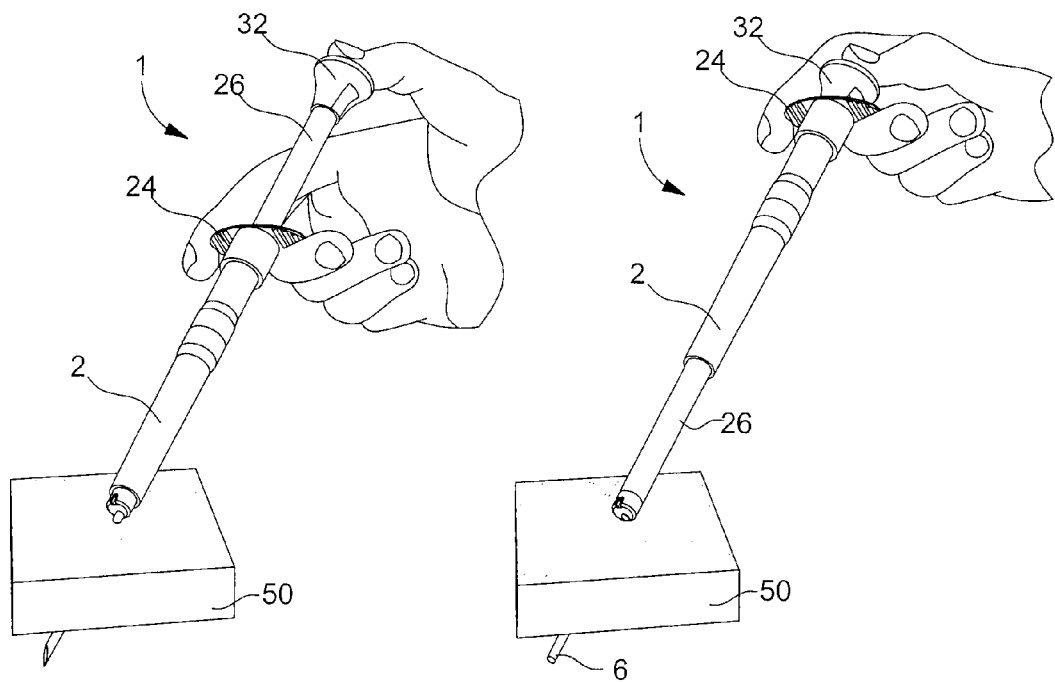

The injection operation is finished when main body 2 has returned to the proximal end position (FIGS. 4D, 5D). During the return upward movement of main body 2 relative to main body 26, the top face of holding part 10 of needle 4 meets head 38 of piston rod 36 which it blocks. As during the downward movement of main body 2, blocking means 34 carried by secondary body 26 will move past head 38 of piston rod 36 by elastically deforming to allow the upward movement of said main body 2 to continue (see FIG. 7). Finally, main body 2 is irreversibly locked onto secondary body 26 via blocking means 48. It will be noted that the space requirement of injection device 1 is the same before and after use, which facilitates in particular handling by the practitioner and storage.

We will now examine the blocking and locking of injection device 1 according to the invention respectively before and after use, in conjunction with FIGS. 8A, 8B and 9A, 9B.

Figure 8A:
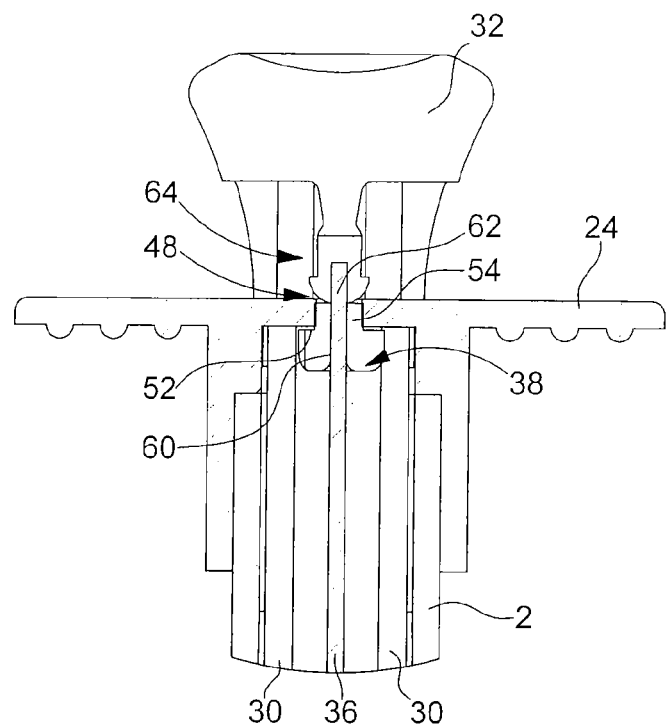
FIGS. 8A, 8B are longitudinal cross-sectional views of the proximal end of the injection device which illustrate the temporary blocking of the secondary body in one direction relative to the main body prior to use.
Figure 8B:
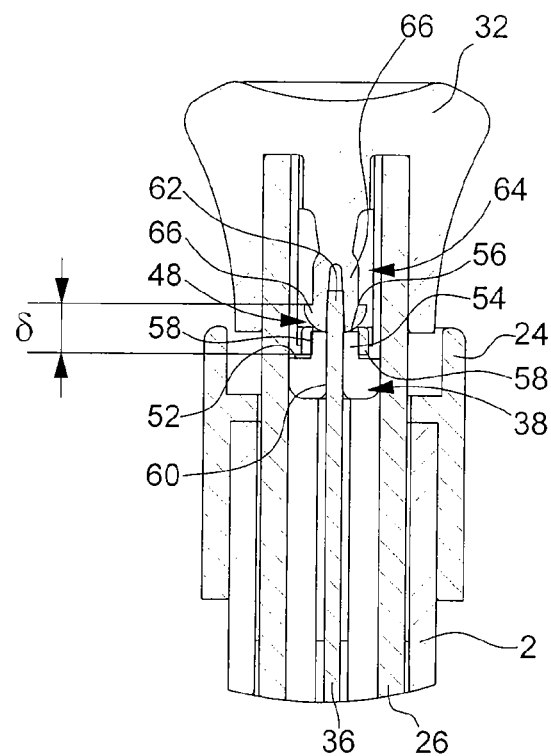
Figure 9A:
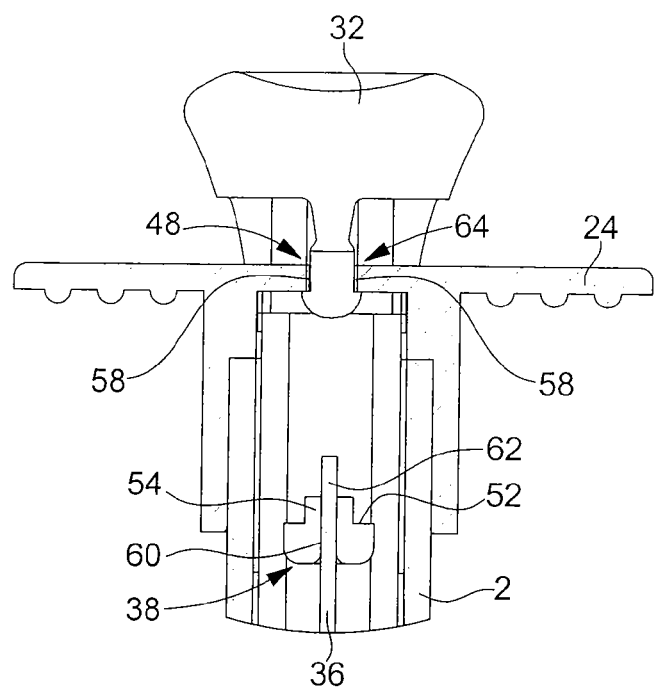
FIGS. 9A, 9B are similar views to those of FIGS. 8A, 8B which illustrate the irreversible locking of the secondary body onto the main body after injection.
Figure 9B:
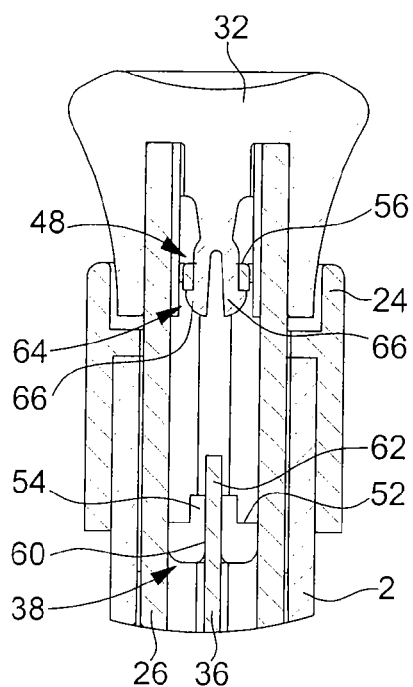
Figure 15:
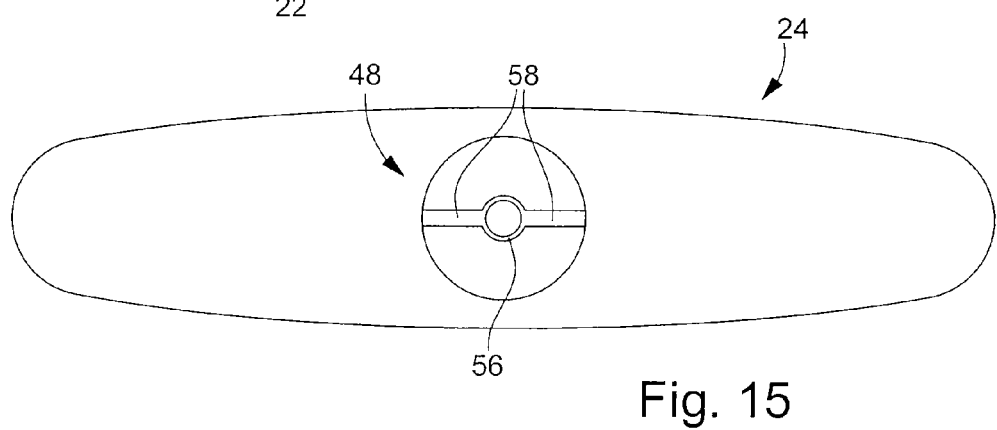
FIG. 15 is a top view of a first embodiment of the means for irreversibly locking the secondary body onto the main body.
Figure 16:
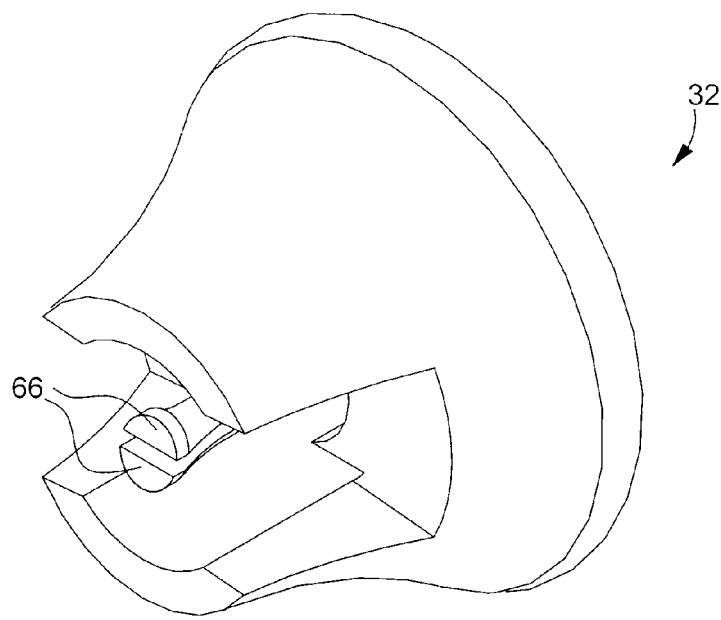
FIG. 16 is a perspective view of a first embodiment of the means provided on the secondary body for blocking the head of the piston rod.

As can be seen upon examining FIGS. 8A and 8B, head 38 of piston rod 36 is a part of general cylindrical shape which has at the proximal end thereof an annular shoulder 52 defining a stud 54 via which head 38 cooperates with blocking means 48 arranged on main body 2. These locking means 48 comprise a circular ring 56 connected to finger rest 24 via at least one and preferably two diametrically opposite radial arms 58 (see also FIGS. 15 and 16). If the injection device does not have a finger rest 24, blocking means 48 could be made integral with main body 2. It will be noted that head 38 has a through hole 60 into which piston rod 36 is fitted such that the proximal end 62 thereof projects therefrom. According to the invention, head 38 of piston rod 36 is engaged by stud 54 in the circular aperture defined by ring 56 and abuts against arms 58 via shoulder 52. At the same time, proximal end 62 of piston rod 62 cooperates with locking means 64, which, according to a preferred but non-limiting embodiment of the invention, are integral with button 32. These locking means 64 comprise, in the example shown in the drawing, a pair of clips 66 between which proximal end 62 of piston rod 62 is engaged. While doing so, end 62 of rod 36 moves clips 66 slightly away from their rest position by elastically deforming them in extension, which prevents clips 66 from penetrating the circular aperture defined by ring 56. Thus, prior to use, injection device 1 according to the invention is blocked in the locking direction, with secondary body 26 unable to be driven into main body 2.

At the start of the injection operation, main body 2 is slid along secondary body 26 to drive needle 4 into skin 50. Main body 2 thus drives therewith piston rod 36 such that end 62 of said rod 36 is released from clips 66, which return to their rest position. At the end of the injection operation, main body 2 is returned to the proximal position thereof by sliding along secondary body 26, piston rod 36 being uncoupled from said main body 2 as described above. Since clips 66 are no longer obstructed by end 62 of piston rod 36, they can cover the distance 5 (see FIG. 8A) separating them from the base of the aperture delimited by ring 56 and penetrate therein by deforming elastically in compression, then returning to the rest position when they emerge from said aperture (see FIGS. 9A and 9B). Thus, after use, secondary body 26 is irreversibly locked onto main body 2, which prevents any subsequent use of injection device 1 according to the invention. Likewise, any risk of needle pricking that could contamination is removed.

According to a preferred embodiment, finger rest part 24 is opaque and head 38 of piston rod 36 is coloured, for example, red. Prior to use of injection device 1, head 38 will thus not be visible, which provides the practitioner with an indication as to the unused state of said device 1. In parallel, the main body 2 could be transparent or opaque and include a window through which head 38 of piston rod 36 would be visible after use, which would indicate to the practitioner that injection device 1 has been discharged.

Figure 10C:
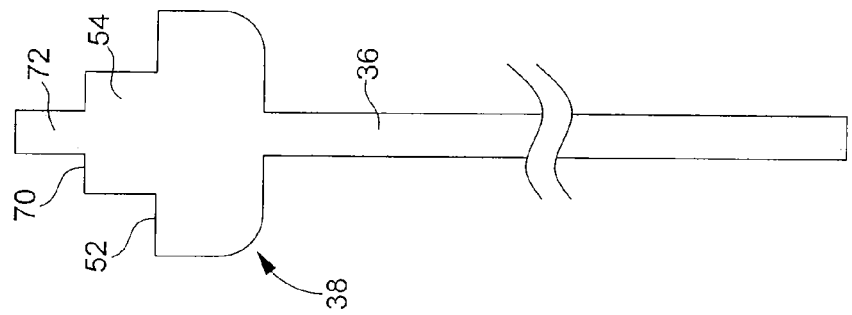
FIGS. 10A, 10B and 10C illustrate various variants of the piston rod.
Figure 10B:
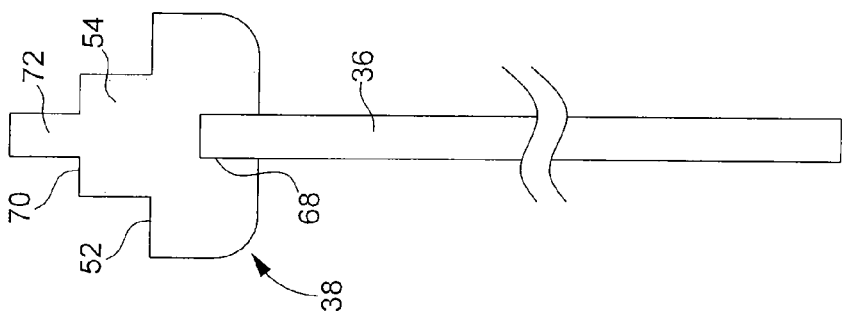
Figure 10A:
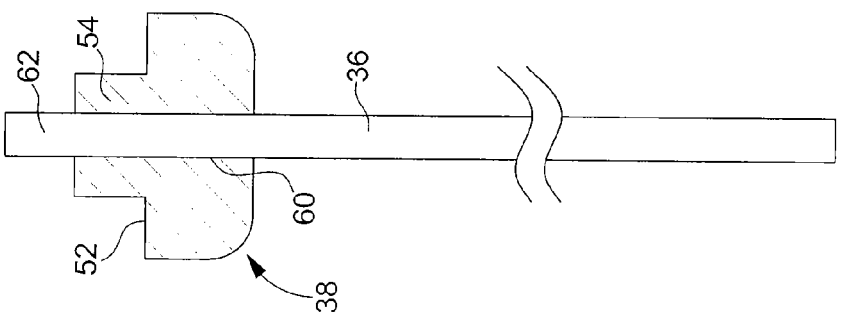

Various variants of piston rod 36 are illustrated in FIGS. 10A to 10C. The variant shown in FIG. 10A has just been described above. It should simply be recalled that head 38 of rod 36 has an annular shoulder defining a stud 54 via which it cooperates with blocking means 48 provided on main body 2, and a through hole 60 into which said rod 36 is fitted such that the proximal end 62 thereof projects therefrom.

According to a second variant illustrated in FIG. 10B, head 38 of piston rod 36 comprises a blind hole 68 in which said rod 36 is engaged. Head 38 further includes an additional shoulder 70, which defines an excrescence 72 that plays the same part, as regards locking means 64, as the proximal end 62 of piston rod 36.

Finally, the piston rod 36 illustrated in FIG. 10C has the same shape and dimensions as that shown in FIG. 10B, the only difference being that head 38 and rod 36 are made in a single piece, for example by plastic injection moulding.

Advantageously, the implant injection devices according to the invention are marketed prefilled. In other words, they already contain the implant to be administered to the patient. In the above description, implant 6 is front loaded, i.e. via the distal end of hollow needle 4, on the side of bevel 8 thereof, because of the presence of clips 66 on the longitudinal axis of symmetry of injection device 1. When the tip of needle 4 is bevelled, front loading carries a risk of the operator being pricked in the case of manual loading, contamination of needle 4, and damage to implant 6 or bevel 8. This is why back loading (proximal end) will be preferred when possible. One embodiment that satisfies these requirements is illustrated in FIGS. 11A, 11B and 12A, 12B.

As can be seen upon examining FIG. 11A, at least two clips 74 have significant penetration resistance (for example from 40 to 60 N and preferably of the order of 50 N) are arranged on the bottom periphery of button 32 or directly on secondary body 26 when the latter is not provided with such means for facilitating gripping. These clips 74 cooperate with retaining elements 76 arranged at the proximal end of main body 2. These retaining elements 76 have the general shape of a reverse L and each comprise a portion at an angle 78, which delimits a cavity 80, open on the inner side of main body 2. The penetration resistance of clips 74 is such that, prior to use of injection device 1, movement of secondary body 26 over a distance Δ relative to main body 2 which would lock clips 74 onto retaining elements 76 is made difficult, unless a force greater than the penetration resistance of clips 76 is exerted. Secondary body 26 thus cannot be inadvertently locked onto main body 2. After carrying out the injection, the practitioner exerts sufficient pressure to lock said clips 74. During this operation, clips 74 slide via the inclined planes 82 thereof onto the edges 84 opposite portions 78 while deforming elastically and return to their initial shape by penetrating cavities 80. It goes without saying that the geometry of the means for locking secondary body 26 onto main body 2 could be reversed, with cavities 80 then open on the outer side of main body 2 and clips 76 gripping retaining elements 76. In this embodiment, piston rod 36 is abutting against implant 6, which prevents the latter from falling. Piston rod 36 thus provides an indication as to the presence of the implant. If implant 6 falls or if injection device 1 is not loaded, piston rod 36 falls via the effect of gravity when injection device 1 is held in the vertical position.

Button 32 can be bonded onto secondary body 26. According to a preferred variant, button 32 is irreversibly secured to secondary body 26 by a lock mechanism using ratchets 86.

Figure 12A:
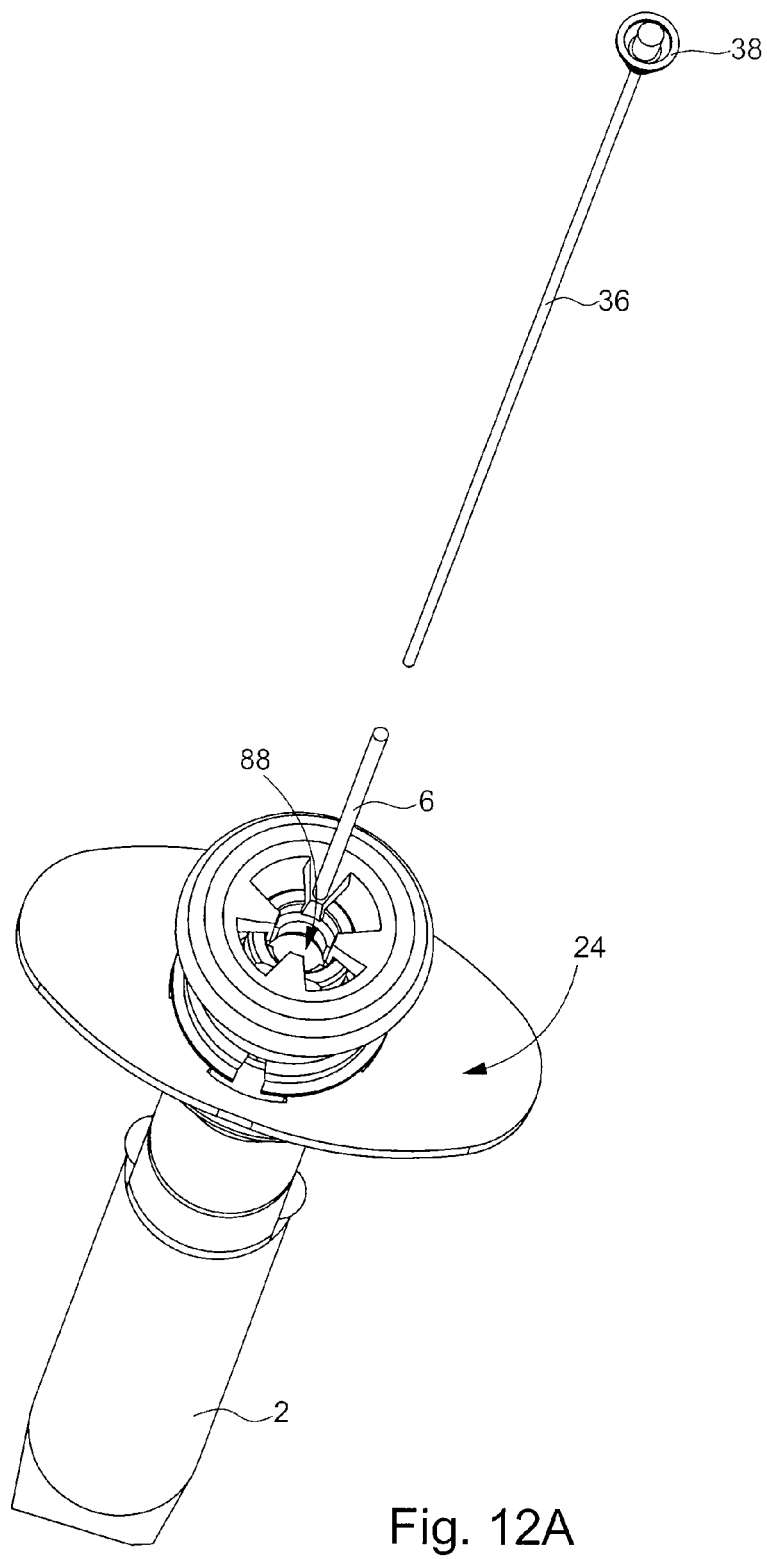
FIG. 12A is a perspective view of the proximal end of the injection device according to the second embodiment showing the loading of the implant and the piston rod.

Owing to this embodiment, wherein the means for locking secondary body 26 onto main body 2 are remote from the centre of injection device 1, one could envisage back loading the device. Button 32 therefore has a through aperture 88 through which implant 6 and piston rod 36 can be successively engaged (FIGS. 12A, 12B). Aperture 12, which passes through holding part 10 of needle 4, will therefore have a the proximal end thereof a cone-shape 90 flaring upwards to facilitate the introduction of said implant 6 and said piston rod 36. Thus, the injection device 1 according to the invention can be delivered to the implant manufacturer with piston rod 36 separate from said device 1. The implant manufacturer will need only to load implant 6 via the proximal end of said device 1 and then introduce said rod 36.

Figure 13A:
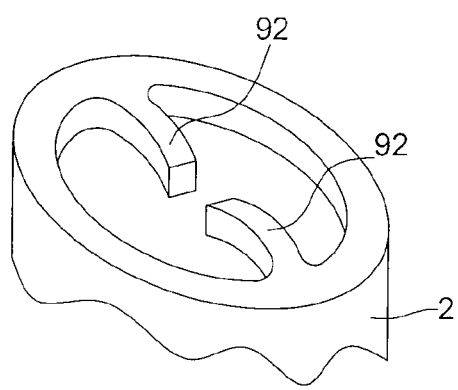
FIG. 13A illustrates a particular embodiment of the top stop member provided at the proximal end of the main body for introducing the piston rod and preventing the removal thereof when the injection device is loaded from the back.
Figure 13B:
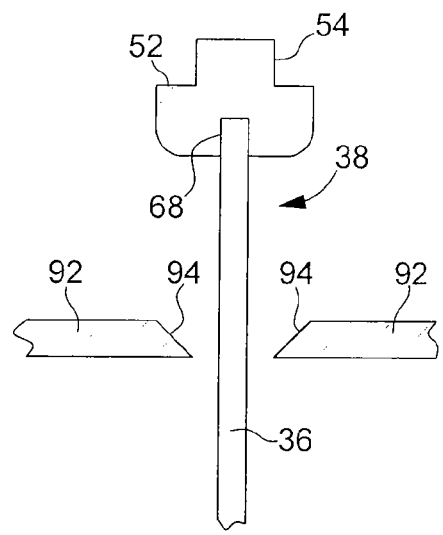
FIGS. 13B, 13C and 13D illustrate various variants of the piston rod compatible with back loading the injection device.
Figure 13C:
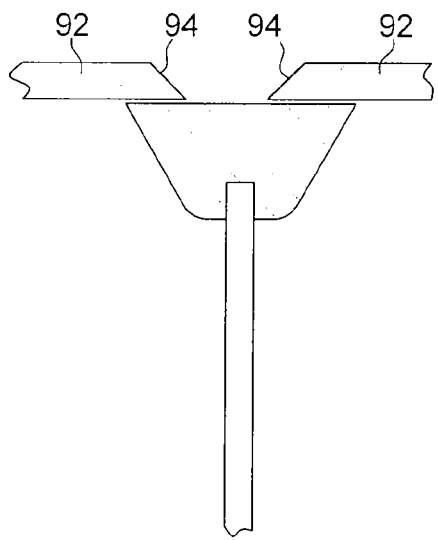
Figure 13D:
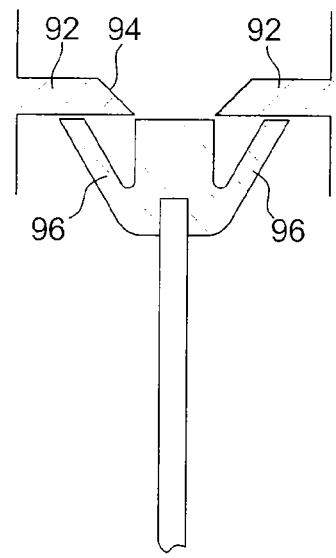

However, once introduced, piston rod 36 must not be able to be removed effortlessly from injection device 1. This can be achieved by giving head 38 of piston rod 36 and the proximal end of main body 2 a geometry preventing such removal. According to a first embodiment (see FIG. 13B), head 38 of rod 36 has a similar shape to that defined above, with the exception that stud 54 is omitted, since it has no function. Head 38 of rod 36 cooperates with two diametrically opposite arms 92 provided at the proximal end of main body 2 and which are elastically deformed downward when head 38 passes (see FIG. 13A). When head 38 has passed arms 92, the latter return to their initial position, preventing piston rod 36 from being removed. In order to facilitate introduction of piston rod 36, arms 92 have two inclined planes 94 in the direction of forward movement of said rod 36. According to a second embodiment (see FIG. 13C), head 38 of piston rod 36 will take a truncated shape and be made of a flexible material, whereas arms 92 will be made using a rigid material. According to a third embodiment, head 38 of piston rod 36 has two inclined arms 96 that converge towards the distal end of injection device 1 and that are elastically deformed when they pass at the height of arms 92 opposite arranged on main body 2 (see FIG. 13D).

As can be seen upon examining FIG. 11B, head 38 of piston rod 36 can have a circular peripheral groove 95 into which inclined planes 94 of arms 92 project. Thus, even in the absence of implant 6, piston rod 36 cannot fall via the effect of gravity when injection device 1 is being held vertically. Likewise, according to this variant, head 38 of piston rod 36 has at the base thereof a stud 97 adapted in shape and dimension to be housed in the cone-shaped aperture 90 in aperture 12 made in holding part 10 at the proximal end thereof. Thus, after implant 6 has been injected, piston rod 36 is immobilised on holding part 10. Finally, main body 2 has an external peripheral edge 99 arranged such that the space left free between this edge 99 and finger rest part 24 is such that it prevents the passage of clips 74 prior to activation of injection device 1.

According to a preferred embodiment, finger rest part 24 is opaque and includes a window through which head 38 of piston rod 36 will appear, indicating to the practitioner that the injection device 1 is loaded. Indeed, since piston rod 36 is free in needle 4 and only abutting against implant 6, the head 38 thereof will only appear in the display window made in secondary body 26 if said implant 6 is present in said needle 4. After injection, head 38 of piston rod 36 will appear in a second window made in the opaque main body 2 to indicate to the practitioner that injection device 1 has been used and is thus empty. One could also arrange a window extending from the position occupied by head 38 of piston rod 36 when injection device 1 is loaded to the position said head 38 occupies when said injection device 1 is empty. Consequently, it would be possible to visualise the progression of the back-injection operation.

According to a variant of the invention, means 64 for irreversibly locking secondary body 26 onto main body 2 after injection of implant 6 could be combined with, or replaced by a cam path type system 98. This cam path 98 is devised such that, while allowing main body 2 to move from the proximal position to the distal position and back, it prevents the inadvertent locking of secondary body 26 onto main body 2 prior to injection while still allowing locking after injection device 1 according to the invention has been used. If the cam path type locking system 98 is used in combination with the locking means 64 described above, it reinforces, from a mechanical point of view, the definitive immobilisation of secondary body 26 on main body 2 after injection, making any reuse of injection device 1 or simply access to needle 4 practically impossible, without destroying injection device 1.

In the example shown in the drawing (see FIG. 17B and the following Figures), cam path 98 is arranged on the external lateral surface of secondary body 26, extending generally rectilinearly parallel to the longitudinal axis of symmetry of secondary body 26. Cam path 98 cooperates with flexible means, for example in the form of an elastic tongue 100, arranged in main body 2 and which is capable of being deformed transversely on either side of cam path 98. Of course, cam path 98 could also be arranged on the inner face of main body 2 and tongue 100 could be integral with secondary body 26.

Cam path 98, which elastic tongue 100 can leave only when injection device 1 is used normally, in other words without being forced, is devised such that, when said injection device 1 is in the start position prior to injection, elastic tongue 100 is in a rest position, wedged in a housing 102 (see FIGS. 17B and 17C). This housing 102 has a section that extends substantially perpendicularly to the general direction of cam path 98 and which prevents main body 2 moving backwards in the direction of secondary body 26. Consequently, it is impossible for secondary body 26 to be inadvertently locked onto main body 1 via the locking means 64 described above when the latter are provided. Housing 102 also has a ramp 106 which leads tongue 100 onto cam path 98.

When main body 2 starts to slide along secondary body 26, elastic tongue 100 exits housing 102 via ramp 106 and starts to move along camp path 98 (see FIGS. 18B and 18C). Because of ramp 106, which it has been forced to follow in order to exit housing 102, tongue 100 is moved away from its rest position and is stressed elastically. Gradually as it progresses along cam path 98, elastic tongue 100 passes one or several notches 108 provided at different places along said cam path 98 to inform the practitioner that the injection process and penetration of needle 4 into the patient's skin 50 are proceeding properly. Likewise, these notches 108 prevent the back-injection gesture being carried out before needle 4 has been completely driven into tissue 50. Each time that tongue 100 falls into a notch 108, it exits again via a ramp 110.

When main body 2 reaches its end distal position and needle 4 has completely penetrated the patient's skin 50, tongue 100 reaches the end of path 98 at a point 112 called the point of return where it expands abruptly and passes to the other side of said cam path 98 (see FIGS. 19B and 19C). In order to make the passage of elastic tongue 100 to the other side of cam path 98 irreversible, at the point of return 112 thereof, the path has a ramp 114, which temporarily brings said tongue 100 into a stressed position such that, when tongue 100 reaches said point of return 112, the tongue temporarily returns to a rest position to then be stressed again on the other side of cam path 98 once it has passed the point of return 112. Tongue 100 passing point of return 112 coincides with the moment that piston rod 36 detaches from main body 2.

When main body 2 returns from its distal position to its proximal position, which coincides with the gradual withdrawal of needle 4 from the patient's skin 50, elastic tongue 100 travels, in the opposite direction, a parallel path to that which it took during the phase of penetration of needle 4 into tissue 50 (see FIGS. 20B and 20C).

Tongue 100 continues its travel until the moment when main body 2 has returned to its proximal start position in which secondary body 26 can lock onto said main body 2 if locking means 64 have been provided for such purpose. At the same moment, elastic tongue 100 reaches a housing 116 in which it is blocked in the rest position (see FIGS. 21B and 21C).

Advantageously, injection device 1 according to the invention can, with certain adaptations, be automated by the addition of a helical spring 118 as illustrated in FIGS. 22A to 22D.

According to this embodiment, injection device 1' includes a hollow main body 2' to which there is permanently fixed, to the distal part 120 thereof, a hollow needle 4' into which an implant 6' is introduced for injection.

The hollow main body 2' is able to slide along a secondary body 26', which is also hollow, arranged coaxially inside said main body 2' and surrounding needle 4' at least until bevel 8' thereof.

Injection device 1' includes finally a piston rod 36' able to slide inside hollow needle 4' and which is used for maintaining implant 6 at the correct depth in tissue 50. This piston rod 36' includes a head 38' fitted with blocking means 122 for cooperating with a corresponding blocking member 124 provided at the proximal end of secondary body 26'.

Piston rod 36' can only move between a proximal position and a distal position respectively controlled by a top stop member 44' and a bottom stop member 46' arranged on main body 2'. In the example shown in the drawing, top stop member 44' is formed by the closed proximal end of main body 2' against which piston rod 36' abuts via the head 38' thereof. Bottom stop member 46' is arranged at a location on the length of said main body 2', on the inner lateral surface thereof.

Likewise, secondary body 26' can only move between a proximal position and a distal position respectively controlled by a top stop member 126 and a bottom stop member 128. In the example shown in the drawing, top stop member 126 is formed by the closed proximal end of secondary body 2' and bottom stop member 128 is formed by means 130 for irreversibly locking secondary body 26' onto main body 2'.

Figures 22A, 22B, 22C, 22D:
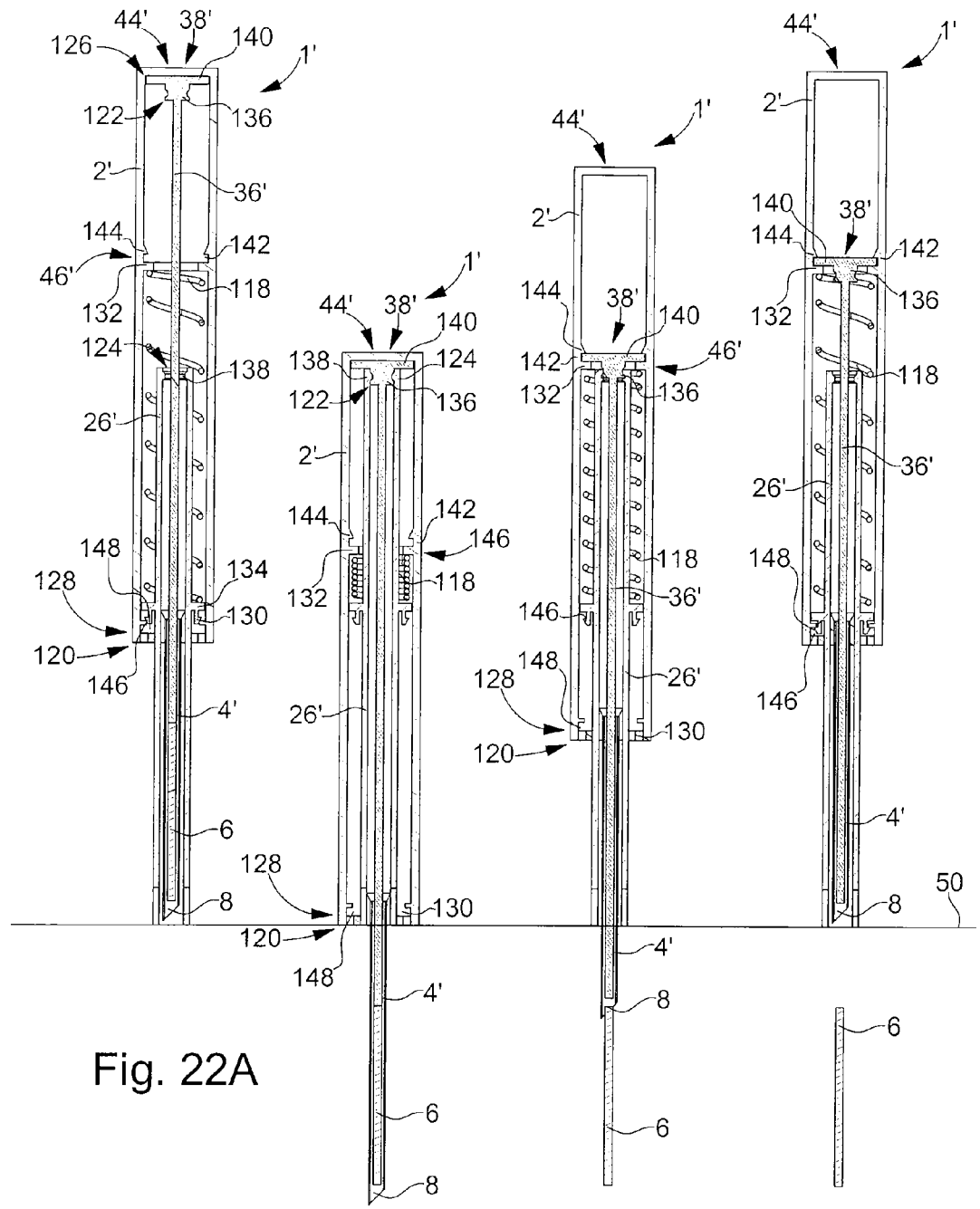
FIGS. 22A to 22D illustrate the various operating phases of a second embodiment of the injection device according to the invention.

The operation of injection device 1' according to the invention is as follows. In FIG. 22A, injection device 1' is shown as it is delivered to the practitioner, with secondary body 26' surrounding needle 4' as far as the bevel 8' thereof, such that any risk of scratching is avoided. Likewise, needle 4' remains invisible to the patient. While holding injection device 1' in one hand via the main body 2' thereof, the practitioner presses the distal end of secondary body 26' against the patient's skin 50. When injection device 1' is suitably arranged, the practitioner exerts pressure on main body 2'. Via the effect of this pressure, main body 2' starts to slide axially along secondary body 26', allowing needle 4', which is secured to said main body 2', to penetrate skin 50. At the same time, main body 2' drives piston rod 36', which is abutting against the closed proximal end of said main body 2', such that the relative position of said rod 36' relative to needle 4' and to implant 6' remains unchanged. Likewise, spring 118, arranged coaxially around secondary body 26' is held axially between an annular shoulder 132 provided on the inner lateral surface of main body 1' and a collar 1234 provided at the distal of secondary body 26' compresses.

When needle 4' is completely driven into tissue 50 (see FIG. 22B), secondary body 26' has been blocked via means 124 thereof onto the corresponding blocking means 122 of piston rod 36'. As can be seen upon examining the drawings, head 38' of piston rod 36' has a generally cylinder shaped body comprising close to the base thereof a circular recess forming a bead 136, which snap fits by deforming elastically into a corresponding aperture 138 arranged at the proximal end of secondary body 26'. In this position, spring 118 is compressed.

In FIG. 22C, the practitioner gradually releases the pressure exerted on main body 2'. Spring 118 is let down, driving therewith secondary body 26', which itself drives piston rod 36'. Thus, piston rod 36' gradually penetrates hollow needle 4' to maintain implant 6 at the correct depth in tissue 50. This movement continues until piston rod 36' is blocked against bottom stop member 46'. As can be seen upon examining the drawings, head 38' of piston rod 36' comprises at the tip thereof a circular plate 140 of substantially equal diameter to the inner diameter of main body 1' and which is housed in a groove 142 delimited by a raised portion 144 and annular shoulder 132.

In FIG. 22D, the injection operation has finished. Spring 118 is again let down, having meshed secondary body 26' with irreversible locking means 130. More specifically, secondary body 26' includes at the distal end thereof at least one and preferably two clicks 146, which deform elastically and mesh under a edge 148 provided on the inner lateral wall of main body 2', towards the distal end thereof. Unless injection device 1' is forced and destroyed, it is definitively locked and cannot be reused. Needle 4' is again surrounded by secondary body 26', such that any risk of contamination by scratching is prevented. Prior to use, the inadvertent locking of clicks 146 under edge 148 could be avoided by adding a cam path type mechanism similar to that described previously.

Figure 23A:
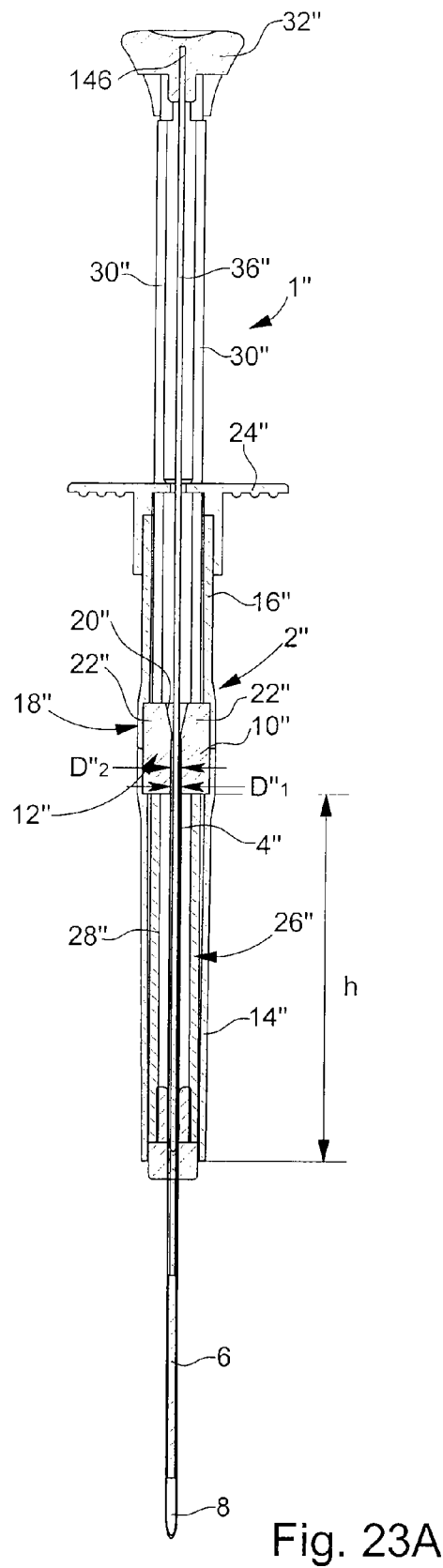
FIGS. 23A and 23B are longitudinal cross-sections respectively before and after use, of a simplified variant of the injection device according to the invention.
Figure 23B:
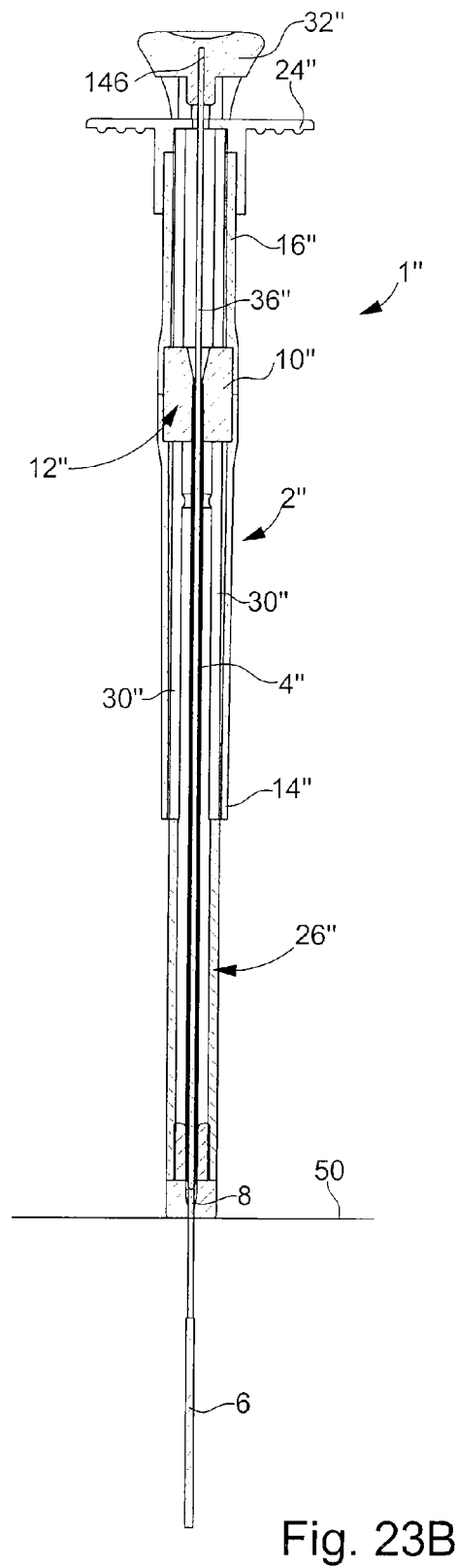

A simplified variant of injection device 1 according to the invention is shown with reference to FIGS. 23A and 23B.

Designated as a whole by the general reference numeral 1", the injection device comprises a hollow main body 2" to which there is permanently fixed a hollow needle 4" into which an implant 6" is introduced for injection. Preferably, hollow needle 4" has at the distal end thereof a bevel 8" whose geometry is adapted to the application envisaged for injection device 1" and, in particular, to the method of administration.

At the proximal end thereof, hollow needle 4" is fixedly mounted in a holding part 10". According to a first variant, holding part 10" is integral with hollow main body 2". According to a second variant shown in the drawing, holding part 10" is used as a joining part to bottom 14" and top 16" tubular parts which form hollow main body 2" and into which said holding part 10" is driven. A through aperture 12" is made in holding part 10" for mounting hollow needle 4". This through aperture 12" has a first part of diameter D", equal to or slightly greater than the external diameter of needle 4" for engaging the proximal end thereof in holding part 10". The first part of diameter $D''_1$ of through aperture 12" is followed by a second part of diameter $D''_2$ smaller than the external diameter of needle 4" for holding the latter in holding part 10" by friction. Finally, the second part of diameter $D''_2$ of through aperture 12" is followed by a cone-shaped third part which flares out in the direction of the proximal end of injection device 1" according to the invention.

Holding part 10" comprises an external lateral wall 18", which delimits an inner volume into which through aperture 12" extends axially. Through aperture 12" is embodied by a tube section 20" which is connected to the external wall 18" at least one and preferably two diametrically opposite radial ribs 22".

Advantageously, the proximal end of main body 2" is fitted with a finger rest part 24" integral with said main body 2" or taking the form of an added part.

The main body 2" is able to slide along a secondary body 26", which is also hollow, arranged coaxially inside said main body 2" and partially surrounding needle 4". This secondary body 26" takes the general form of a tube 28" provided with two diametrically opposite rectilinear slots 30" which extend from the proximal end of tube 29" to a height h above the distal end of said tube 28". The proximal end of tube 28" will advantageously be fitted with means facilitating the gripping of injection device 1" such as a button 32". This button 32" could be integral with secondary body 26" or made in the form of an added part.

Injection device 1" according to the invention includes finally a piston rod 36" capable of sliding inside hollow needle 4" and used for holding implant 6 at the correct depth in tissue 50. This piston rod 36" is secured to secondary body 26" by being driven or bonded via the proximal end thereof in a blind hole 146 made in button 32".

The operating principle of injection device 1" described above is as follows. In FIG. 23A, injection device 1" is shown as it is delivered to the practitioner, with needle 4" in the out position. Main body 2" occupies the distal end position controlled by radial ribs 22" which are abutting against the bottom of slots 30". Holding the injection device 1" in one hand via the main body 2" thereof, the practitioner drives needle 4" into tissue 50. Once needle 4" is completely driven into tissue 50, the practitioner will carry out a back injection operation. Placing his thumb on button 32", the practitioner controls the upward movement of main body 2" by pulling on finger rest 24", which he is holding with his index and middle fingers. The upward movement of main body 2" is accompanied by the gradual withdrawal of needle 4" from tissue 50. Simultaneously, piston rod 36" is driven into needle 4" to maintain implant 6 at the correct depth in tissue 50. The injection operation is finished when main body 2" reaches the proximal end position against button 32" (see FIG. 23B).

FIGS. 24A to 24D illustrate schematically another mechanism for irreversibly locking secondary body 26 onto main body 2. This mechanism essentially comprises a ring 149 arranged freely between main body 2 and secondary body 26.

Figure 24A:
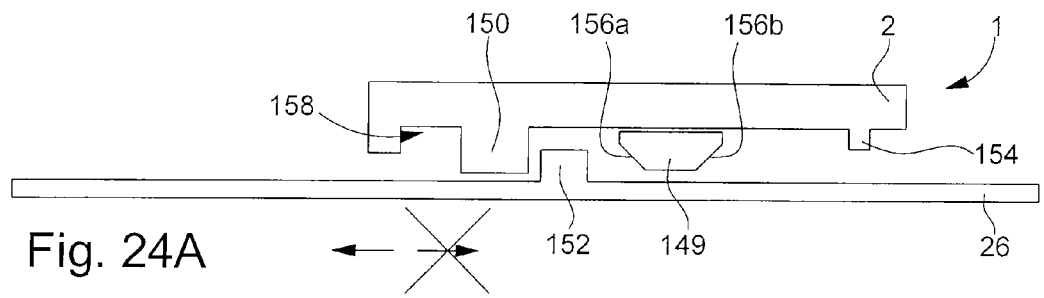
FIGS. 24A to 24D are schematic diagrams that illustrate the operating principle of a variant of the means for locking the secondary body onto the main body.

In FIG. 24A, injection device 1 is shown as it is delivered to the practitioner. In this position, main body 2 cannot move upwards in the direction of secondary body 26, which prevents any inadvertent locking of said main body 2 onto said secondary body 26. Indeed, main body 2 has on the inner lateral surface thereof a slot 150, which abuts against a corresponding slot 152 provided on the outer lateral surface of secondary body 26.

Figure 24B:
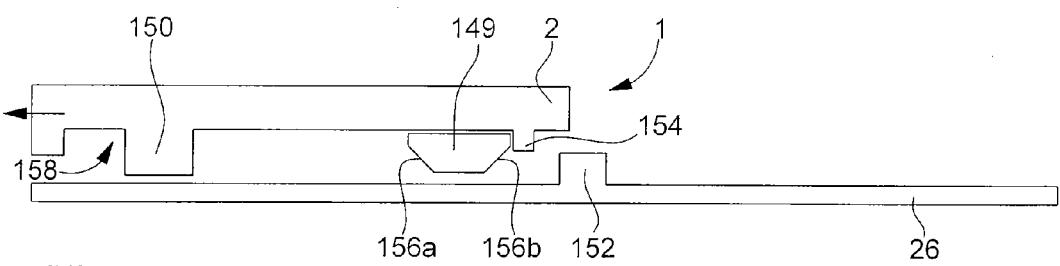

When the needle starts to penetrate the skin (not shown), main body 2 slides along secondary body 26, driving therewith ring 149 via an additional slot 154 provided on the inner lateral surface thereof (FIG. 24B). When ring 149 is stopped against slot 152, the latter deforms elastically and passes under said ring 149. This movement is facilitated by the presence of an inclined plane or ramp 156a provided on ring 149 and along which slot 152 can slide.

Figure 24C:
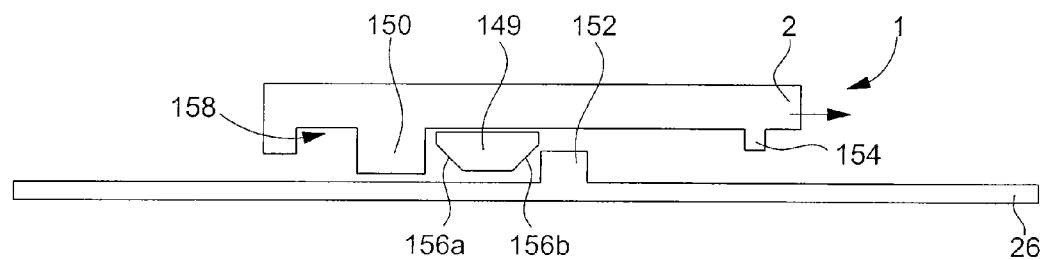
Figure 24D:
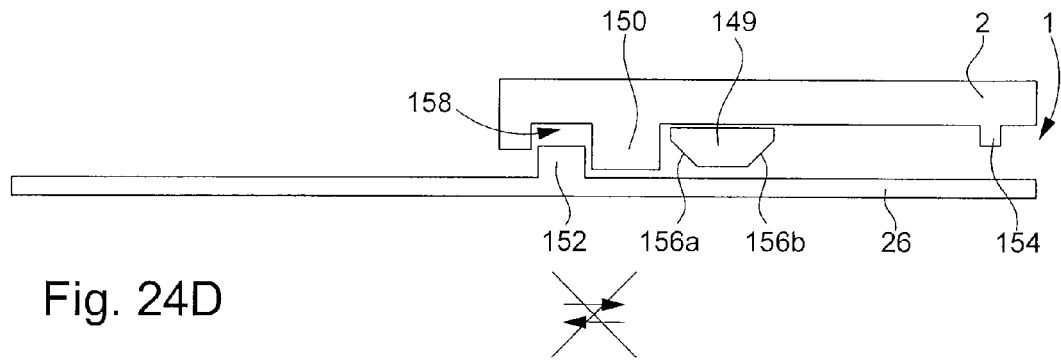

When the needle is completely driven into the skin and main body 2 has reached the end distal position, the back injection operation can start (FIG. 24C). Main body 2 moves up along secondary body 26 driving therewith ring 149 via the slot 150 thereof in the opposite direction to previously until said ring 148 is stopped against slot 152 of secondary body 26. At that moment, slot 152 deforms elastically passing in succession under ring 149, and under slot 150 and returns to its initial shape housed in a cavity 158 arranged on the inner lateral surface of main body 2 (FIG. 24D). This movement is facilitated by the presence of a second ramp 156b provided on ring 149 and along which slot 152 can slide. At this stage, main body 2 and secondary body 26 are irreversibly locked in translation and injection device 1 cannot be reused.

It goes without saying that the present invention is not limited to the embodiments that have just been described, and that various simple alterations and variants can be envisaged by those skilled in the art without departing from the scope of the claims annexed to this Patent Application.

What is claimed is:

1. A back injection device for injecting an implant into tissue, comprising:
    (a) a hollow main body movable from a distal position, prior to injection, to a proximal position, after injection;
    (b) a hollow needle permanently fixed to the hollow main body and having a hollow space into which the implant is introducable;
    (c) a secondary body arranged coaxially inside the main body and surrounding the entire body of the needle before and after injection;
    (d) a piston rod axially slidable inside the hollow needle; and
    (e) coupling means arranged on the main body, to couple the main body and the piston rod,
    wherein the injection device is movable between the following positions:
        (1) a starting position in which the injection device is pressable against tissue, wherein the implant is introduced into the hollow space of the needle, wherein the secondary body surrounds the entire body of the needle;
        (2) an injection position in which the main body is moved along the secondary body from the proximal position to the distal position to allow the needle to extend beyond the secondary body so as to be penetrable into tissue, wherein the coupling means couples the main body and the piston rod so that the movement of the main body is accompanied by a concomitant movement of the piston rod, until the main body reaches the distal end so as to allow the needle to reach a maximum extension or penetration in tissue;
        (3) a back injection position in which the coupling means is released from the piston rod, thereby causing the main body to move from the distal position toward the proximal position so as to allow the needle to retract, wherein the piston rod remains fixed and is positioned to maintain the implant at a required position even as the needle is retracted; and
        (4) an end position in which the main body returns from the distal position to the proximal position so that the piston rod and the needle completely retract into the secondary body, wherein the secondary body surrounds the entire body of the needle.

2. Injection device according to claim 1, wherein the relative position of the piston rod and the implant remains unchanged during positions (1)-(3).

3. Injection device according to claim 1, wherein the relative position of the piston rod and the hollow needle remains unchanged during the movement of the main body from the proximal position to the distal position, and wherein the piston rod is driven into the needle when the main body returns from the distal position to the proximal position.

4. Injection device according to claim 1, wherein the piston rod can only move between a proximal and a distal position respectively controlled by a top stop member and a bottom stop member arranged on the main body.

5. Injection device according to claim 4, wherein the piston rod includes a head via which the rod cooperates with the top and bottom stop members.

6. Injection device according to claim 5, wherein the piston rod is driven by the main body when the latter moves from the proximal position to the distal position, and wherein said piston rod is uncoupled from said main body in the back injection position (3).

7. Injection device according to claim 6, wherein in the back injection position (3), the piston rod remains fixed relative to said main body, and said rod is retained by blocking means provided on the secondary body.

8. Injection device according to claim 7, wherein the blocking means can move past the piston rod when the latter is stopped against the top stop member or the bottom stop member.

9. Injection device according to claim 8, wherein the blocking means are able to deform elastically when they move past the piston rod.

10. Injection device according to claim 7, wherein the piston rod cooperates via the end thereof with the blocking means of the secondary body.

11. Injection device according to claim 10, wherein the blocking means take the form of a bead provided on the inner lateral face of the secondary body.

12. Injection device according to claim 5, wherein the main body can only move between a proximal position and a distal position, which are respectively controlled by a top stop member and a bottom stop member arranged on the secondary body.

13. Injection device according to claim 12, wherein the needle is fixed to the main body via a holding part.

14. Injection device according to claim 13, wherein the holding part includes a tube portion, which delimits a through aperture for fixing the needle and which is connected to the main body by at least one rib.

15. Injection device according to claim 14, wherein the top stop member arranged on the secondary body is formed by a button provided at the proximal end of the secondary body, and wherein the bottom stop member arranged on the secondary body is defined by the ribs which abut against the bottom of longitudinal rectilinear slots provided on the secondary body and which extend from the proximal end of said secondary body to a height above the distal end thereof.

16. Injection device according to claim 13, wherein the top stop member arranged on the main body is formed by means that block the secondary body on the main body after injection, and wherein the bottom stop member arranged on the main body is formed by the holding part.

17. Injection device according to claim 16, wherein the blocking means include a circular ring connected to the main body by at least one radial arm and against which the head of the piston rod abuts, the proximal end of said head projecting into the ring.

18. Injection device according to claim 17, wherein the injection device further comprises means for irreversibly locking the secondary body onto the main body after injection.

19. Injection device according to claim 18, wherein the locking means include a pair of clips arranged on the secondary body and between which the proximal end of the head of the piston rod is engaged to prevent said clips from penetrating the circular ring prior to use of the injection device, said clips no longer being moved by said proximal end of the head of the piston rod after use of the injection device and thus being able to project into the aperture defined by the circular ring to lock the secondary body onto the main body.

20. Injection device according to claim 5, wherein it can be loaded from the proximal end side of the main body.

21. Injection device according to claim 20, wherein at least two clips arranged on the secondary body cooperate with retaining elements arranged at the proximal end of the main body for irreversibly locking the secondary body onto the main body after use of the injection device.

22. Injection device according to claim 20, wherein the secondary body includes a button having a through aperture through which the implant and the piston rod can be engaged in succession.

23. Injection device according to claim 20, wherein the head of the piston rod and the proximal end of the main body are arranged so as to prevent the removal of said piston rod once the latter has been introduced into the main body.

24. Injection device according to claim 5, wherein the injection device includes a cam path system for irreversibly locking the secondary body onto the main body.

25. Injection device according to claim 24, wherein the injection device includes an elastic tongue, which cooperates with the cam path.

26. Injection device according to claim 25, wherein prior to use, the tongue is blocked in a housing so as to prevent the secondary body being inadvertently locked onto the main body.

27. Injection device according to claim 25, wherein, when the needle starts to penetrate the tissue, the elastic tongue moves along one side of the cam path while being stressed elastically, reaches a point of return where the elastic tongue is let down and where the elastic tongue passes to the other side of said cam path at the moment when the needle has completely penetrated the tissue, then again moves along the cam path in the opposite direction to the previous direction while being stressed elastically when the needle is withdrawn from the tissue until the moment when the elastic tongue reaches a housing in which the elastic tongue is blocked in the rest position, thereby irreversibly locking the secondary body onto the main body.

28. Injection device according to claim 25, wherein the injection device includes an irreversible locking mechanism with a ring.

29. Injection device according to claim 28, wherein the ring is freely arranged between the main body and the secondary body and cooperates with slots respectively provided on the inner lateral surface of the main body and on the external lateral surface of the secondary body.

30. Injection device according to claim 29, wherein when the needle starts to penetrate the tissue, the main body drives the ring via the slot until said ring is stopped against the slot, the latter then deforming elastically and passing under the ring, and wherein when the needle is withdrawn from the tissue, the main body drives the ring via the slot thereof in the opposite direction until said ring is stopped against the slot of the secondary body, the slot then deforming elastically and passing in succession under the ring and under the slot and returning to the initial shape thereof while lodging in a cavity arranged on the inner lateral surface of the main body.

31. Injection device according to claim 5, wherein the injection device includes a spring coaxially arranged around the secondary body and held axially between the main body and the secondary body.

32. Injection device according to claim 31, wherein the spring is held axially between an annular shoulder provided on the inner lateral surface of the main body and a collar provided at the distal end of the secondary body.

33. Injection device according to claim 31, wherein, when the main body moves from the proximal position to the distal position, the spring is compressed and the head of the piston rod is blocked on the secondary body such that when the main body returns to the proximal position, the spring is let down, driving therewith the secondary body, which itself drives the piston rod.

34. Injection device according to claim 33, wherein the head of the piston rod is provided with blocking means for cooperating with corresponding blocking means provided at the proximal end of the secondary body.

35. Injection device according to claim 34, wherein the blocking means is formed by a bead which fits into a corresponding aperture arranged at the proximal end of the secondary body.

36. Injection device according to claim 31, wherein the top stop member is formed by the proximal end of the main body and wherein the bottom stop member is arranged at a location on the length of said main body, on the inner lateral surface thereof.

37. Injection device according to claim 36, wherein the top stop member is formed by a groove in which the head of the piston rod lodges.

38. Injection device according to claim 31, wherein the secondary body can only move between a proximal position and a distal position respectively controlled by a top stop member and a bottom stop member.

39. Injection device according to claim 38, wherein the top stop member is formed by the proximal end of the main body and wherein the bottom stop member is formed by means for irreversibly locking the secondary body onto the main body.

40. Injection device according to claim 39, wherein locking means include at least one pawl provided a the distal end of the secondary body and which is meshed under an edge provided on the inner lateral wall of the main body.

41. Injection device according to claim 5, wherein the main body is opaque and includes a window through which the head of the piston rod is visible after use, which will indicate whether the injection device has been discharged.

42. Injection device according to claim 5, wherein the finger rest part is opaque and includes a window through which the head of the piston rod appears prior to injection, indicating that the injection device is loaded, and wherein the head of the piston rod appears in a second window made in the opaque main body to indicate whether said injection device has been used and is thus empty.

43. Injection device according to claim 5, wherein a window extends from the position occupied by the head of the piston rod when the injection device is loaded to a position occupied by said head when said injection device is empty.

* * * * *